United States Patent
Dhawan et al.

(10) Patent No.: US 11,236,040 B2
(45) Date of Patent: *Feb. 1, 2022

(54) MULTIPLE CHARGED IONIC COMPOUNDS DERIVED FROM POLYAMINES AND COMPOSITIONS THEREOF AND METHODS OF PREPARATION THEREOF

(71) Applicant: Ecolab USA Inc., Saint Paul, MN (US)

(72) Inventors: Ashish Dhawan, Saint Paul, MN (US); Carter M. Silvernail, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/554,415

(22) Filed: Aug. 28, 2019

(65) Prior Publication Data

US 2020/0071261 A1 Mar. 5, 2020

Related U.S. Application Data

(60) Provisional application No. 62/724,357, filed on Aug. 29, 2018.

(51) Int. Cl.
*C07C 229/16* (2006.01)
*C07C 237/06* (2006.01)

(52) U.S. Cl.
CPC .......... *C07C 229/16* (2013.01); *C07C 237/06* (2013.01)

(58) Field of Classification Search
CPC ........................... C07C 229/16; C07C 237/06
See application file for complete search history.

(56) References Cited

U.S. PATENT DOCUMENTS

| | | | |
|---|---|---|---|
| 3,794,586 A | 2/1974 | Kimura et al. |
| 4,259,217 A | 3/1981 | Murphy |
| 4,355,071 A | 10/1982 | Chang |
| 4,705,665 A | 11/1987 | Malik |
| 4,784,797 A | 11/1988 | Treybig et al. |
| 5,053,150 A | 10/1991 | Emert et al. |
| 5,192,798 A | 3/1993 | Aiken et al. |
| 5,399,746 A | 3/1995 | Steiger et al. |
| 5,462,714 A | 10/1995 | Talwalker et al. |
| 5,614,616 A | 3/1997 | Buysch et al. |
| 5,670,464 A | 9/1997 | Kita et al. |
| 5,738,795 A | 4/1998 | Chen |
| 6,004,466 A | 12/1999 | Derian et al. |
| 6,054,054 A | 4/2000 | Robertson et al. |
| 6,080,323 A | 6/2000 | Yu et al. |
| 6,090,754 A | 7/2000 | Chan et al. |
| 6,503,880 B1 | 1/2003 | Skold et al. |
| 6,797,785 B1 | 9/2004 | Hund et al. |
| 6,881,710 B1 | 4/2005 | O'Lenick, Jr. et al. |
| 7,052,614 B2 | 5/2006 | Barak |
| 7,084,129 B1 | 8/2006 | Smith et al. |
| 7,345,015 B1 | 3/2008 | Kong et al. |
| 7,507,399 B1 | 3/2009 | O'Lenick, Jr. |
| 7,604,978 B2 | 10/2009 | Eldridge |
| 8,324,264 B1 | 12/2012 | Eldridge et al. |
| 8,933,055 B2 | 1/2015 | Pedersen et al. |
| 9,388,361 B2 | 7/2016 | Terada et al. |
| 9,956,153 B2 | 5/2018 | Emiru et al. |
| 10,850,999 B2 | 12/2020 | DiMascio et al. |
| 10,945,431 B2 | 3/2021 | Karandikar et al. |
| 2001/0044393 A1 | 11/2001 | Peterson, Jr. et al. |
| 2002/0155978 A1 | 10/2002 | Man et al. |
| 2003/0121532 A1 | 7/2003 | Coughlin et al. |
| 2005/0215461 A1 | 9/2005 | Gluck et al. |
| 2006/0008496 A1 | 1/2006 | Kulkarni et al. |
| 2006/0289164 A1 | 12/2006 | Smith et al. |
| 2006/0289359 A1 | 12/2006 | Manek et al. |
| 2008/0152567 A1 | 6/2008 | Killough |
| 2010/0004316 A1 | 1/2010 | Lu et al. |
| 2010/0029530 A1 | 2/2010 | Whiteley |
| 2010/0305014 A1 | 12/2010 | Miralles et al. |
| 2010/0331234 A1 | 12/2010 | Mahon et al. |
| 2011/0112007 A1 | 5/2011 | Hodge et al. |
| 2012/0053111 A1 | 3/2012 | Hodge et al. |
| 2012/0070341 A1 | 3/2012 | Eder et al. |
| 2012/0115962 A1 | 5/2012 | Lee et al. |
| 2012/0258157 A1 | 10/2012 | Koltzenburg et al. |
| 2013/0266669 A1 | 10/2013 | Jiang et al. |
| 2014/0124454 A1 | 5/2014 | Nichols et al. |
| 2014/0224733 A1 | 8/2014 | Osness et al. |
| 2015/0203738 A1 | 7/2015 | Witham et al. |

(Continued)

FOREIGN PATENT DOCUMENTS

| CN | 101972612 A | 2/2011 |
|---|---|---|
| CN | 102504247 A | 6/2012 |

(Continued)

OTHER PUBLICATIONS

Fan et al., "Synthesis and Aggregation Behavior of a Hexameric Quaternary Ammonium Surfactant", Langmuir, vol. 27, pp. 10570-10579, Jul. 28, 2011.

Kawakami et al., "Antibacterial Activity of Radial Compounds with Peripheral Quaternary Ammonium Units", Transactions of the Materials Research Society of Japan, vol. 35[4], pp. 885-887, 2010.

Zhang et al., "PAMAM-Based Dendrimers with Different Alkyl Chains Self-Assemble on Silica Surfaces: Controllable Layer Structure and Molecular Aggregation", J. Phys. Chem. B, vol. 122, pp. 6648-6655, Jun. 13, 2018.

Zhou et al., "Cooperative binding and self-assembling behavior of cationic low molecular-weight dendrons with RNA molecules", Organic & Biomolecular Chemistry, vol. 4, pp. 581-585, 2006.

Brycki et al., "The biodegradation of monomeric and dimeric alkylammonium surfactants", Journal of Hazardous Materials, vol. 280, pp. 797-815, Aug. 6, 2014.

(Continued)

*Primary Examiner* — Sikarl A Witherspoon
(74) *Attorney, Agent, or Firm* — McKee, Voorhees & Sease, PLC

(57) ABSTRACT

Disclosed herein are the multiple charged cationic or anionic compounds, methods of making thereof, and articles or compositions comprising thereof. The disclosed multiple charged cationic or anionic compounds are derived from polyamines through two reactions: an aza-Michael addition with an activated olefin having an ionic group and a ring-opening reaction with an epoxide.

25 Claims, 4 Drawing Sheets

(56) References Cited

U.S. PATENT DOCUMENTS

| | | |
|---|---|---|
| 2015/0290100 A1 | 10/2015 | Eder et al. |
| 2016/0010035 A1 | 1/2016 | Liu et al. |
| 2016/0030315 A1 | 2/2016 | Emiru et al. |
| 2016/0145610 A1 | 5/2016 | Lu et al. |
| 2016/0262999 A1 | 9/2016 | Pedersen et al. |
| 2016/0264744 A1 | 9/2016 | Boday et al. |
| 2017/0029691 A1 | 2/2017 | Faust, Jr. et al. |
| 2017/0121560 A1 | 5/2017 | Dockery et al. |
| 2017/0233643 A1 | 8/2017 | Agashe et al. |
| 2017/0349543 A1 | 12/2017 | Siegwart et al. |
| 2017/0360040 A1 | 12/2017 | Kost et al. |
| 2018/0007895 A1 | 1/2018 | Karandikar et al. |
| 2018/0066211 A1 | 3/2018 | Pickering et al. |
| 2018/0105629 A1 | 4/2018 | Tada et al. |
| 2018/0118999 A1 | 5/2018 | Hikem et al. |
| 2018/0163020 A1 | 6/2018 | Zong et al. |
| 2019/0062187 A1 | 2/2019 | Dhawan et al. |
| 2019/0223434 A1 | 7/2019 | Balasubramanian et al. |
| 2019/0224627 A1 | 7/2019 | Glanz et al. |
| 2020/0071205 A1 | 3/2020 | Dhawan et al. |
| 2020/0071261 A1 | 3/2020 | Dhawan et al. |
| 2020/0332423 A1 | 10/2020 | Dhawan et al. |

FOREIGN PATENT DOCUMENTS

| | | |
|---|---|---|
| CN | 102675535 A | 9/2012 |
| CN | 103288672 A | 9/2013 |
| CN | 102675535 B | 11/2013 |
| CN | 104130335 A | 11/2014 |
| CN | 104130351 A | 11/2014 |
| CN | 105076201 A | 11/2015 |
| CN | 105523956 A | 4/2016 |
| CN | 106172434 A | 12/2016 |
| CN | 106423269 A | 2/2017 |
| CN | 106423284 A | 2/2017 |
| CN | 106634929 A | 5/2017 |
| CN | 106946743 A | 7/2017 |
| CN | 107440935 A | 12/2017 |
| CN | 108033895 A | 5/2018 |
| CN | 108048249 A | 5/2018 |
| CN | 108938662 A | 12/2018 |
| EP | 0296441 A2 | 12/1988 |
| GB | 847321 | 9/1960 |
| GB | 1550420 A | 8/1979 |
| JP | 6116351 A | 4/1994 |
| JP | 6116898 A | 4/1994 |
| JP | 2001187751 A | 7/2001 |
| JP | 2007054710 A | 3/2007 |
| JP | 2012136504 A | 7/2012 |
| JP | 2014009177 A | 1/2014 |
| JP | 2014093768 A | 5/2014 |
| JP | 2014221859 A | 11/2014 |
| WO | 2004056843 A2 | 7/2004 |
| WO | 2012083497 A1 | 6/2012 |
| WO | 2013087287 A1 | 6/2013 |
| WO | 2014079621 A1 | 5/2014 |
| WO | 2015084304 A1 | 6/2015 |
| WO | 2016205513 A1 | 12/2016 |
| WO | 2017003639 A2 | 1/2017 |
| WO | 2017201076 A1 | 11/2017 |
| WO | 2018112548 A1 | 6/2018 |
| WO | 2019046409 A1 | 3/2019 |

OTHER PUBLICATIONS

Gan et al., "Sugar-Based Ester Quaternary Ammonium Compounds and Their Surfactant Properties", Journal of Surfactants and Detergents, vol. 17, Issue 3, pp. 465-470, Jan. 3, 2014.

Negm et al., "Synthesis, Characterization and Biological Activity of Sugar-Based Gemini Cationic Amphiphiles", Journal of Surfactants and Detergents, vol. 11, Issue 3, pp. 215-221, Apr. 26, 2008.

Tan et al., "The use of quaternised chitosan-loaded PMMA to inhibit biofilm formation and downregulate the virulence-associated gene expression of antibiotic-resistant *Staphylococcus*", Biomaterials, vol. 33, Issue 2, pp. 365-377, Jan. 2012.

Zaky, Mohamad, "Biocidal Activities of Cationic Surface Active Starch and Its Transition Metal Complexes Against Different Bacterial Strains", Journal of Surfactants and Detergents, vol. 13, Issue 3, pp. 255-260, Jul. 2010.

Zhi et al., "Self-aggregation and antimicrobial activity of saccharide-cationic surfactants", Colloids and Surfaces: A Physicochemical and Engineering Aspects, vol. 456, pp. 231-237, Aug. 2014.

Zhang et al., "Controllable Self-Assembly of Amphiphilic Dendrimers on a Silica Surface: The Effect of Molecular Topological Structure and Salinity", Journal of Physical Chemistry, vol. 8, pp. 10990-10999, Oct. 5, 2016.

Zhang et al., "Supporting information", Beijing National Laboratory for Molecular Sciences, published with Controllable Self-Assembly of Amphiphilic Dendrimers on a Silica Surface, 4 pages, Oct. 5, 2016.

Ecolab USA Inc., in connection with PCT/US2019/048451 filed Aug. 28, 2019, "The International Search Report and the Written Opinion of the International Searching Authority, or the Declaration", 22 pages, dated Jan. 29, 2020.

"Azamethonium", http://pubchem.ncbi.nlm.nih.gov/compound/9383, last modified Oct. 6, 2018 and accessed by Applicant Oct. 11, 2018.

Zielinski et al., "Synteza nowych czwartorzedowych soli amoniowych do organofilizacji nanokompozytowych napelniaczy polimerowych", www.miesiecznikchemik.pl, 2007.

International Preliminary Examining Authority in connection with PCT/US2019/048451 filed Aug. 28, 2019, "The International Preliminary Report of Patentability", 29 pages, dated Sep. 7, 2020.

Somerscales, Euan F.C., "Fundamentals of Corrosion Fouling", Experimental Thermal and Fluid Science, vol. 14, pp. 335-355, 1997.

Zielinksi, Wojciech et al., "TI—Synthesis of new quaternary ammonium salts for organophilization of fillers for polymeric nanocomposites", D1: Database Chemical Abstracts [Online] chemical abstracts; XP55789968, Database accession No. 2007:1236240 Jan. 1, 2007.

Labade et al., "Cesium fluoride catalyzed Aza-Michael addition reaction in aqueous media", Monatsh Chem., vol. 142, pp. 1055-1059, Jul. 19, 2011.

Bi et al., "Dendrimer-Based Demulsifiers for Polymer Flooding Oil-in-Water Emulsions", Energy Fuels, vol. 31. No. 5, pp. 5395-5401, Apr. 20, 2017.

Krämer et al., "Dendritic polyamines: simple access to new materials with defined treelike structures for application in nonviral gene delivery", Chembiochem, vol. 5(8), pp. 1081-1087, Aug. 6, 2004.

Miller et al., "Non-viral CRISPR/Cas gene editing in vitro and in vivo enabled by synthetic nanoparticle co-delivery of Cas9 mRNA and sgRNA", Angew Chem Int Ed Engl., vol. 56(4), pp. 1059-1063, Jan. 19, 2017.

Ning et al., "Synthesis and characterization of a novel non-polyether demulsifier", Chemical Engineer, 3 pages, 2013.

Wang et al., "A novel environment-sensitive biodegradable polydisulfide with protonatable pendants for nucleic acid delivery", Journal of Controlled Release, vol. 120, pp. 250-258, May 11, 2007.

Step-1

Step-2

Step-1

Step-2

Wherein

US 11,236,040 B2

MULTIPLE CHARGED IONIC COMPOUNDS DERIVED FROM POLYAMINES AND COMPOSITIONS THEREOF AND METHODS OF PREPARATION THEREOF

CROSS-REFERENCE TO RELATED APPLICATIONS

This application claims priority under 35 U.S.C. § 119 to provisional application Ser. No. 62/724,357, filed Aug. 29, 2018, herein incorporated by reference in its entirety.

FIELD OF THE INVENTION

The present disclosure relates generally to the field of multiple charged molecules and methods of making the same. In particular, the present disclosure relates to a new class of modified polyamines that comprise both cationic or anionic groups and nonionic groups attached to its nitrogen atoms. The disclosed compounds can be useful as a fouling control agents, antimicrobials, sanitizers, fabric softeners, antistatic agents, corrosion inhibitors, foaming agents, floatation collectors, dispersants, surfactants assisted enhanced oil recovery (EOR), cleaners, etc., alone or together with other chemicals in various applications.

BACKGROUND OF THE INVENTION

A water system, including an industrial water system, serves many different purposes. Any water system, including its equipment and water, is prone to microbial contamination and fouling. Fouling or deposition of any organic or inorganic material can occur even in an industrial water system that is treated with the best water treatment programs currently available. If a water system is not periodically cleaned or treated, then it will become heavily fouled.

Fouling occurs due to microbiological contamination and subsequently microbial and/or biofilm growth. Sources of microbial contamination in industrial water systems are numerous and may include, but are not limited to, air-borne contamination, water make-up, process leaks, and improperly cleaned equipment. Microorganisms causing fouling can establish their microbial communities on any wetable or semi-wetable surfaces of a water system. Evaporative cooling water systems are particularly prone to fouling.

Fouling has a negative impact on a water system, particularly an industrial water system. For example, severe mineral scale (inorganic material) would buildup on any water contact surfaces and any scale in turn provides an ideal environment for microorganism and/or biofilm growth. If fouling or biofilm growth can progress in a water system, the water system can suffer from decreased operational efficiency, premature equipment failure, and increased health-related risks associated with microbial fouling and/or biofilm growth.

Exopolymeric substances secreted by microorganism aid formation of biofilms as the microbial communities develop on surfaces. These biofilms are complex ecosystems that establish a means for concentrating nutrients and offer protection for microbial growth, so the biofilms can accelerate scale formation, corrosion, and other fouling processes. Not only do biofilms contribute to efficiency reduction of the water system, but they also provide an excellent environment for microbial proliferation and for generating dangerous *Legionella* bacteria. It is therefore important that biofilms and other fouling processes be reduced to the greatest extent possible to minimize the health-related risk associated with *Legionella* and other water-borne pathogens.

Various methods are developed to clean or to remove biofilms and microorganisms associated with the biofilms. While cleaning and removing biofilms are necessary, a better approach is to prevent or reduce fouling or biofilm formation or growth, so the need to clear or remove biofilms is reduced. Cleaning or removing biofilms usually requires operation interruption and introduction of other chemicals. One way to prevent or reduce fouling and/or biofilm formation or growth is to treat a water system with a fouling control composition agent or fouling control composition. For example, corrosion inhibitors and/or fouling control composition agents are often added into upstream oil and gas production fluids to protect carbon steel pipelines and infrastructure from corrosion and biofilm growth.

Quaternary ammonium compounds have been used for many years as corrosion inhibitors and fouling control agents. Quaternary ammonium compounds belong to an important subcategory of surfactants because they have unique properties. A main distinction between quaternary ammonium compounds from other surfactants is their unique structure. Quaternary ammonium compounds consist mainly of two moieties, a hydrophobic group, e.g., long alkyl group, and a quaternary ammonium salt group. The unique positive charge of the ammonium plays a key role, e.g., electrostatic interactions, between the surfactant and surface or different components of biofilms. However, the quaternary ammonium compounds used for such purpose are often bis quaternary species or species quaternized with benzyl chloride that are known to be very hazardous. In additional, governmental regulations exist to release any water containing single quaternary compounds into the environment.

Therefore, it is an objective of the disclosure to develop a method to make the novel compounds for fouling control in a water system efficiently and effectively.

It is a further objective of the disclosure to use the novel compounds in an article, product, and/or composition.

These and other objects, advantages and features of the present disclosure will become apparent from the following specification taken in conjunction with the claims set forth herein.

BRIEF SUMMARY OF THE INVENTION

Disclosed herein are novel compounds, methods of making the disclosed compounds, and articles or compositions comprising the disclosed compounds. More particularly, the disclosed compounds are multiple charged cationic or anionic compounds comprising multiple positive or negative charges and nonionic groups within single molecule of various sizes. They are derived from water soluble polyamine or polyethyleneimines.

In one aspect, disclosed herein is a multiple charged compound having one of the generic formula of $NA_2$-[$R^{10'}$]$_n$-$NA_2$, $(RNA)_n$-$RNA_2$, $NA_2$-$(RNA)_n$-$RNA_2$, or $NA_2$-$(RN(R'))_n$-$RNA_2$, wherein $R^{10'}$ is a linear or branched, unsubstituted or substituted $C_2$-$C_{10}$ alkylene group, or combination thereof; R is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkylene group, or combination thereof; R' is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkyl group, RNAB, RNARNAB, or RN(RNAB)$_2$; n can be from 2 to 1,000,000; A is a combination of H,

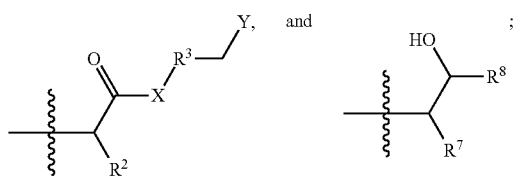

or a combination of H,

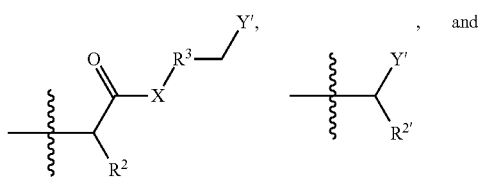

wherein X is NH or O; $R^2$ is H, $CH_3$, or an unsubstituted, linear or branched $C_2$-$C_{10}$ alkyl, alkenyl, or alkynyl group; $R^{2'}$ is H, $CH_3$, or an unsubstituted or substituted, linear or branched $C_1$-$C_{10}$ alkyl, alkenyl, alkynyl group, —COOH, —$CH_2COOH$, Y', or —$(CH_2)_m$—Y'; m is an integer of 2 to 4; $R^3$ is absent or an unsubstituted, linear or branched $C_1$-$C_{30}$ alkylene group; Y is —$NR_4R_5R_6^{(+)}$; Y' is —COOH, —$SO_3H$, —$PO_3H$, —$OSO_3H$, —$OPO_3H$, or a salt thereof; $R^4$, $R^5$, and $R^6$ are independently a $C_1$-$C_{10}$ alkyl group; $R^7$ is H or alkyl; and $R^8$ is alkyl, or —$(CH_2)_k$—O-alkyl, wherein k is an integer of 1-30; wherein the compound is a multiple charged cationic compound having 1, 2, 3, or more

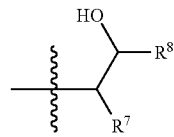

groups and at least one

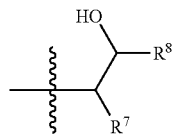

group or a multiple charged anionic compound having 1, 2, 3, or more

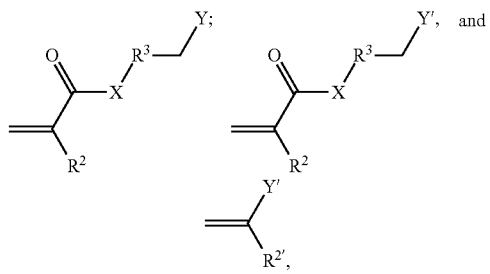

groups, and at least one

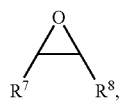

group.

In another aspect, disclosed herein is a multiple charged compound derived from a polyamine through its reactions with an activated olefin and an epoxide, wherein the activated olefin has one of the following formulas;

and the epoxide is wherein X is NH or O; $R^2$ is H, $CH_3$, or an unsubstituted, linear or branched $C_2$-$C_{10}$ alkyl, alkenyl, or alkynyl group; $R^{2'}$ is H, $CH_3$, or an unsubstituted or substituted, linear or branched $C_1$-$C_{10}$ alkyl, alkenyl, alkynyl group, —COOH, —$CH_2COOH$, Y', or —$(CH_2)_m$—Y'; m is an integer of 2 to 4; $R^3$ is absent or an unsubstituted, linear or branched $C_1$-$C_{30}$ alkylene group; Y is —$NR_4R_5R_6^{(+)}$; Y' is —COOH, —$SO_3H$, —$PO_3H$, —$OSO_3H$, —$OPO_3H$, or a salt thereof; $R^4$, $R^5$, and $R^6$ are independently a $C_1$-$C_{10}$ alkyl group; $R^7$ is H or alkyl; and $R^8$ is alkyl, or —$(CH_2)_k$—O-alkyl, wherein k is an integer of 1-30; wherein the polyamine and activated olefin undergo aza Michael Addition reaction and the polyamine and epoxide undergo ring opening reaction; wherein the compound is a multiple charged cationic compound having 1, 2, 3, or more positive charges from the activated olefin and at least one nonionic group from the epoxide or multiple charged anionic compound having 1, 2, 3, or more negative charges from the activated olefin and at least one nonionic group from the epoxide.

In another aspect, disclosed here is a method of making the compound or its salt disclosed here.

In yet another aspect, provided herein is an article, product, or composition that comprises one or more compounds disclosed herein.

The forgoing summary is illustrative only and is not intended to be in any way limiting. In addition to the illustrative aspects, embodiments and features described above, further aspects, embodiments, and features of the present technology will become apparent to those skilled in the art from the following drawings and the detailed description, which shows and describes illustrative embodiments of the present technology. Accordingly, the figures and detailed description are also to be regarded as illustrative in nature and not in any way limiting.

Figure 1:
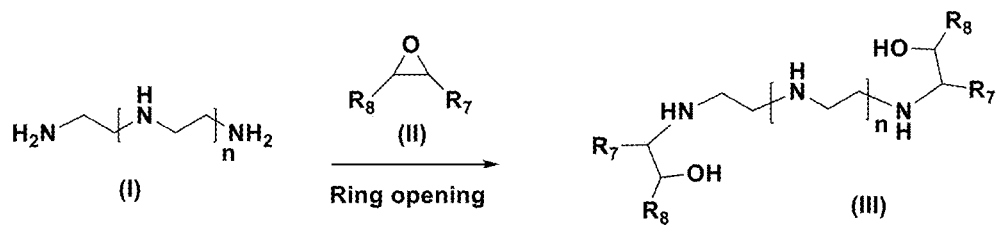
FIG. 1 shows an exemplary generic reaction scheme to produce a multiple charged cationic compound first by a ring-opening reaction between a linear polyethyleneimine and epoxide and then an aza-Michael addition reaction with an activated olefin ($\alpha,\beta$-unsaturated carbonyl compound).
Figure 1:
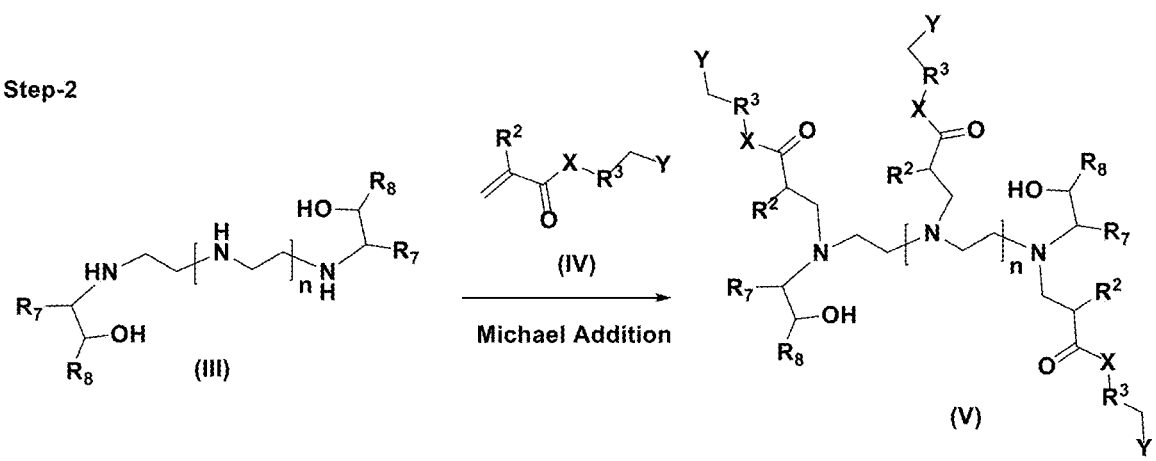

Various embodiments of the present disclosure will be described in detail with reference to the drawings, wherein like reference numerals represent like parts throughout the several views. Reference to various embodiments does not limit the scope of the disclosure. Figures represented herein are not limitations to the various embodiments according to the disclosure and are presented for exemplary illustration of the disclosure.

DETAILED DESCRIPTION OF THE PREFERRED EMBODIMENT

Disclosed herein are novel compounds, methods of making the compounds disclosed herein, and articles or compositions comprising the compounds disclosed herein. More particularly, multiple charge cationic or anionic compounds derived from a polyamine, an activated olefin, and epoxide through both an aza-Michael addition and ring-opening reaction are disclosed. Methods of synthesizing such compounds are disclosed.

The embodiments of this disclosure are not limited to particular compositions and methods of use which can vary and are understood by skilled artisans. It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring and liquid handling procedures used for making concentrates or use solutions in the real world; through error in these procedures; through differences in the manufacture, source, or purity of the ingredients used to make the compositions or carry out the methods; and the like. The term "about" also encompasses amounts that differ due to novel equilibrium conditions for a composition resulting from a particular initial mixture. Whether or not modified by the term "about", the claims include equivalents to the quantities.

As used herein, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, or 6 substituents.

Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having two to about 30 carbon atoms, and further including at least one double bond. In some embodiments, an alkenyl group has from 2 to about 30 carbon atoms, or typically, from 2 to 10 carbon atoms. Alkenyl groups may be substituted or unsubstituted. For a double bond in an alkenyl group, the configuration for the double bond can be a trans or cis configuration. Alkenyl groups may be substituted similarly to alkyl groups.

Alkynyl groups are straight chain, branched, or cyclic alkyl groups having two to about 30 carbon atoms, and further including at least one triple bond. In some embodiments, an alkynyl group has from 2 to about 30 carbon atoms, or typically, from 2 to 10 carbon atoms. Alkynyl groups may be substituted or unsubstituted. Alkynyl groups may be substituted similarly to alkyl or alkenyl groups.

As used herein, the terms "alkylene", "cycloalkylene", "alkynylides", and "alkenylene", alone or as part of another substituent, refer to a divalent radical derived from an alkyl, cycloalkyl, or alkenyl group, respectively, as exemplified by —CH$_2$CH$_2$CH$_2$—. For alkylene, cycloalkylene, alkynylene, and alkenylene groups, no orientation of the linking group is implied.

The term "ester" as used herein refers to —R$^{30}$COOR$^{31}$ group. R$^{30}$ is absent, a substituted or unsubstituted alkylene, cycloalkylene, alkenylene, alkynylene, arylene, aralkylene, heterocyclylalkylene, or heterocyclylene group as defined herein. R$^{31}$ is a substituted or unsubstituted alkyl, cycloalkyl, alkenyl, alkynyl, aryl, aralkyl, heterocyclylalkyl, or heterocyclyl group as defined herein.

The term "amine" (or "amino") as used herein refers to —R$^{32}$NR$^{33}$R$^{34}$ groups. R$^{32}$ is absent, a substituted or unsubstituted alkylene, cycloalkylene, alkenylene, alkynylene, arylene, aralkylene, heterocyclylalkylene, or heterocyclylene group as defined herein. R$^{33}$ and R$^{34}$ are independently hydrogen, or a substituted or unsubstituted alkyl, cycloalkyl, alkenyl, alkynyl, aryl, aralkyl, heterocyclylalkyl, or heterocyclyl group as defined herein.

The term "amine" as used herein also refers to an independent compound. When an amine is a compound, it can be represented by a formula of R$^{32'}$NR$^{33'}$R$^{34'}$ groups, wherein R$^{32''}$ R$^{33'}$, and R$^{34}$ are independently hydrogen, or a substituted or unsubstituted alkyl, cycloalkyl, alkenyl, alkynyl, aryl, aralkyl, heterocyclylalkyl, or heterocyclyl group as defined herein.

The term "alcohol" as used herein refers to —R$^{35}$OH groups. R$^{35}$ is absent, a substituted or unsubstituted alkylene, cycloalkylene, alkenylene, alkynylene, arylene, aralkylene, heterocyclylalkylene, or heterocyclylene group as defined herein.

The term "carboxylic acid" as used herein refers to —R$^{36}$COOH groups. R$^{36}$ is absent, a substituted or unsubstituted alkylene, cycloalkylene, alkenylene, alkynylene, arylene, aralkylene, heterocyclylalkylene, or heterocyclylene group as defined herein.

The term "ether" as used herein refers to —R$^{37}$OR$^{38}$ groups. R$^{37}$ is absent, a substituted or unsubstituted alkylene, cycloalkylene, alkenylene, alkynylene, arylene, aralkylene, heterocyclylalkylene, or heterocyclylene group as defined herein. R$^{38}$ is a substituted or unsubstituted alkyl, cycloalkyl, alkenyl, alkynyl, aryl, aralkyl, heterocyclylalkyl, or heterocyclyl group as defined herein.

The term "solvent" as used herein refers to any inorganic or organic solvent. Solvents are useful in the disclosed method or article, product, or composition as reaction solvent or carrier solvent. Suitable solvents include, but are not limited to, oxygenated solvents such as lower alkanols, lower alkyl ethers, glycols, aryl glycol ethers and lower alkyl glycol ethers. Examples of other solvents include, but are not limited to, methanol, ethanol, propanol, isopropanol and butanol, isobutanol, ethylene glycol, diethylene glycol, triethylene glycol, propylene glycol, dipropylene glycol, mixed ethylene-propylene glycol ethers, ethylene glycol phenyl ether, and propylene glycol phenyl ether. Water is a solvent too. The solvent used herein can be of a single solvent or a mixture of many different solvents.

Glycol ethers include, but are not limited to, diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether, propylene glycol phenyl ether, and the like, or mixtures thereof.

Acids

The compositions or methods disclosed herein may include an acid. However, in some embodiments, the compositions disclosed herein are free of an acid.

Generally, acids, as used in this disclosure, include both organic and inorganic acids. Organic acids include, but not limited to, hydroxyacetic (glycolic) acid, formic acid, acetic acid, propionic acid, butyric acid, valeric acid, caproic acid, gluconic acid, itaconic acid, trichloroacetic acid, urea hydrochloride, and benzoic acid. Organic acids also include dicarboxylic acids such as oxalic acid, malonic acid, succinic acid, glutaric acid, maleic acid, fumaric acid, adipic acid, and terephthalic acid. Combinations of these organic acids can also be used. Inorganic acids include, but are not limited to, mineral acids, such as phosphoric acid, sulfuric acid, sulfamic acid, methylsulfamic acid, hydrochloric acid, hydrobromic acid, hydrofluoric acid, and nitric acid. Inorganic acids can be used alone, in combination with other inorganic acid(s), or in combination with one or more organic acid. Acid generators can be used to form a suitable acid, including for example generators such as potassium fluoride, sodium fluoride, lithium fluoride, ammonium fluoride, ammonium bifluoride, sodium silicofluoride, etc.

Examples of particularly suitable acids in this the methods or compositions disclosed herein include inorganic and organic acids. Exemplary inorganic acids include phosphoric, phosphonic, sulfuric, sulfamic, methylsulfamic, hydrochloric, hydrobromic, hydrofluoric, and nitric. Exemplary organic acids include hydroxyacetic (glycolic), citric, lactic, formic, acetic, propionic, butyric, valeric, caproic, gluconic, itaconic, trichloroacetic, urea hydrochloride, and benzoic. Organic dicarboxylic acids can also be used such as oxalic, maleic, fumaric, adipic, and terephthalic acid.

Alkalinity Source or Base

The disclosed methods of preparation or compositions may include using an effective amount of an alkalinity source or base as a catalyst or ingredient. The alkalinity source or base in turn comprises one or more alkaline compounds. The alkalinity source can be added to the reaction mixture in the form of solid, liquid, or solution thereof.

In general, an effective amount of the alkalinity source should be considered as an amount that provides a reaction mixture having a pH of at least about 8. When the solution has a pH of between about 8 and about 10, it can be considered mildly alkaline, and when the pH is greater than about 12, the solution can be considered caustic.

The alkalinity source can include an alkali metal carbonate, an alkali metal hydroxide, alkaline metal silicate, alkaline metal metasilicate, or a mixture thereof. Suitable metal carbonates that can be used include, for example, sodium or potassium carbonate, bicarbonate, sesquicarbonate, or a mixture thereof. Suitable alkali metal hydroxides that can be used include, for example, sodium, lithium, or potassium hydroxide. Examples of useful alkaline metal silicates include sodium or potassium silicate (with $M_2O:SiO_2$ ratio of 2.4 to 5:1, M representing an alkali metal) or metasilicate. A metasilicate can be made by mixing a hydroxide and silicate. The alkalinity source may also include a metal borate such as sodium or potassium borate, and the like.

The alkalinity source may also include ethanolamines, urea sulfate, amines, amine salts, and quaternary ammonium. The simplest cationic amines, amine salts and quaternary ammonium compounds can be schematically drawn thus:

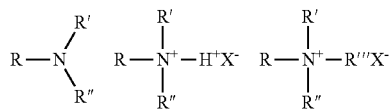

in which, R represents a long alkyl chain, R', R'', and R''' may be either long alkyl chains or smaller alkyl or aryl groups or hydrogen and X represents an anion.

In some embodiments, the methods of preparation are free of the alkalinity source because the reactants contain a primary amine or primary amine group to catalyze the reaction. In some embodiments, the compositions disclosed herein are free of the alkalinity source.

Polyamines

A polyamine can have, but is not limited to, a generic formula of $NH_2-[R^{10'}]_n-NH_2$, $(RNH)_n-RNH_2$, $H_2N-(RNH)_n-RNH_2$, or $H_2N-(RN(R'))_n-RNH_2$, wherein $R^{10'}$ is a linear or branched, unsubstituted or substituted $C_2$-$C_{10}$ alkylene group, or combination thereof; R is $-CH_2-$, $-CH_2CH_2-$, $-CH_2CH_2CH_2-$, $-CH(CH_3)CH_2-$, a linear or branched, unsubstituted or substituted $C_4$-$C_{10}$ alkylene group, or combination thereof; R' is $-CH_2-$, $-CH_2CH_2-$, $-CH_2CH_2CH_2-$, $-CH(CH_3)CH_2-$, a linear or branched, unsubstituted or substituted $C_4$-$C_{10}$ alkyl group, $RNH_2$, $RNHRNH_2$, or $RN(RNH_2)_2$; and n can be from 2 to 1,000,000. The monomer in a polyamine, e.g., the R or R' group, can be the same or different. In this disclosure, a polyamine refers to both small molecule polyamine when n is from 1 to 9 and polymeric polyamine when n is from 10 to 1,000,000.

Small molecule polyamines include, but are not limited to ethylenediamine, diethylenetriamine, triethylenetetramine, tetraethylenepentamine, pentaethylenehexamine, hexaethyleneheptamine, and tris(2-aminoethyl)amine.

Other possible polyamines include JEFFAMINE® monoamines, diamines, and triamines by Huntsman. These highly versatile products contain primary amino groups attached to the end of a polyether backbone normally based on propylene oxide (PO), ethylene oxide (EO), or a mixture of both oxides. JEFFAMINE® amines include a polyetheramine family consisted of monoamines, diamines and triamines based on the core polyether backbone structure. JEFFAMINE® amines also include high-conversion, and polytetramethylene glycol (PTMEG) based polyetheramines. These JEFFAMINE® amines have an average molecular weight $(M_w)$ of from about 130 to about 4,000.

A polyamine used in this disclosure can be a polyamine derivative or modified polyamine, in which one or more of the NH protons, but not all, in the polyamine is substituted by an unsubstituted or substituted group. For example, an alkyl polyamine that contains one or more alkyl group connected to the nitrogen atom can be used to produce the multiple charge cationic polyamine disclosed herein. In these PEI derivatives, only some of primary $NH_2$ or secondary NH protons are replaced by other non-proton groups and the remaining $NH_2$ or NH protons can still react with a Michael acceptor, such as an activated olefin containing a hydrophilic (ionic) group, by an aza-Michael Addition reaction.

One class of the polymeric polyamine includes polyethyleneimine (PEI) and its derivatives. Polyethyleneimine (PEI) or polyaziridine is a polymer with a repeating unit of $CH_2CH_2NH$ and has a general formulation of $NH_2(CH_2CH_2NH)_n-CH_2CH_2NH_2$, wherein n can be from 2 to $10^5$. The repeating monomer in PEI has a molecular weight $(M_w)$ of 43.07 and a nitrogen to carbon ratio of 1:2.

PEI derivatives include ethoxylated/propylated PEIs, polyquats PEI, polyglycerol quats PEI, and other PEI derivatives, salts, or mixtures thereof. The molar mass of the polyethyleneimines, including modified polyethyleneimines can vary from about 800 g/mol to about 2,000,000 g/mol. For Example, SOKALAN® HP20 is an alkoxylated PEI product. In these PEI derivatives, only some of primary $NH_2$ or secondary NH protons are replaced by functional groups and the remaining $NH_2$ or NH protons can still react with a Michael acceptor, e.g., activated olefin or $\alpha,\beta$-unsaturated compound containing a hydrophilic (ionic) group.

PEIs and their derivatives can linear, branched, or dendric. Linear polyethyleneimines contain all secondary amines, in contrast to branched PEIs which contain primary, secondary and tertiary amino groups. Totally branched, dendrimeric forms also exist and contain primary and tertiary amino groups. Drawings for unmodified linear, branched, and dendrimeric PEI are shown below.

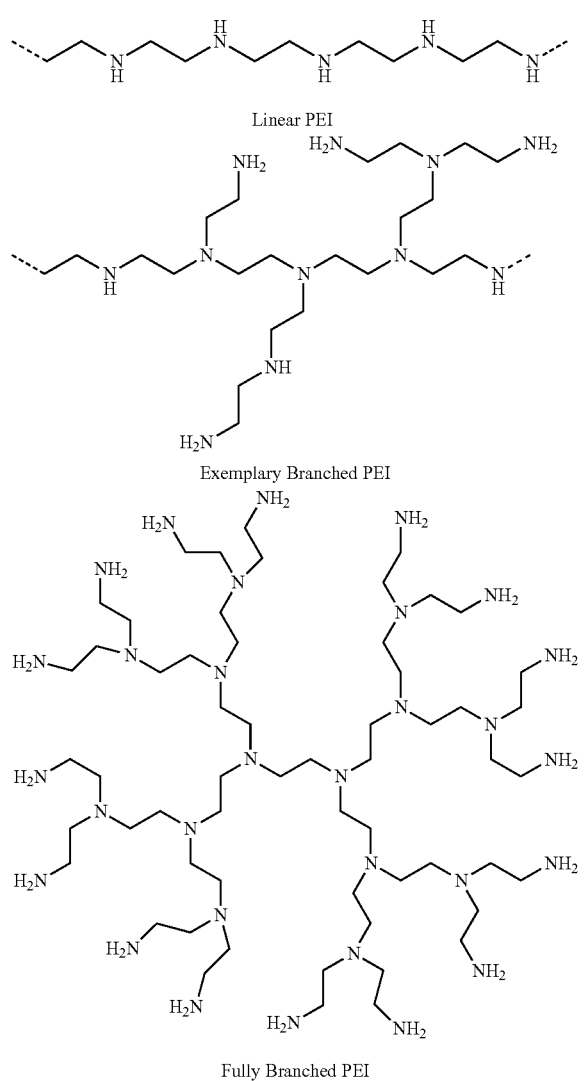

Linear PEI

Exemplary Branched PEI

Fully Branched PEI

PEI derivatives are usually obtained by substituting proton(s) on the nitrogen atoms with different group. One such PEI derivative is ethoxylated and propoxylated PEI, wherein the polyethyleneimines are derivatized with ethylene oxide (EO) and/or propylene oxide (PO) side chains. Ethoxylation of PEIs can increase the solubility of PEIs.

PEI is produced on industrial scale. Various commercial polyethyleneimines are available, including for example those sold under the tradename Lupasol® (BASF), including for example Lupasol® FG, Lupasol® G, Lupasol® PR 8515, Lupasol® WF, Lupasol® G 20/35/100, Lupasol® HF, Lupasol® P, Lupasol® PS, Lupasol® PO 100, Lupasol® PN 50/60, and Lupasol® SK. These PEIs have average molecular weights ($M_w$) of about 800, about 1,300, about 2,000, about 5,000, about 25,000, about 1,300/2,000/5,000, about 25,000, about 750,000, about 750,000, about 1,000,000, and about 2,000,000, respectively.

Two commonly used averages for molecular weight of a polymer are number average molecular weight ($M_n$) and weight average molecular weight ($M_w$). The polydispersity index (D) represents the molecular weight distribution of the polymers. $Mn=(\Sigma n_i M_i)/\Sigma n_i$, $M_w=(\Sigma n_i M_i^2)/\Sigma n_i M_i$, and $D=M_w/M_n$, wherein the index number, i, represents the number of different molecular weights present in the sample and $n_i$ is the total number of moles with the molar mass of $M_i$. For a polymer, $M_n$ and $M_w$ are usually different. For example, a PEI compound can have a $M_n$ of about 10,000 by GPC and $M_w$ of about 25,000 by LS.

Light Scattering (LS) can be used to measure $M_w$ of a polymer sample. Another easy way to measure molecular weight of a sample or product is gel permeation chromatography (GPC). GPC is an analytical technique that separates molecules in polymers by size and provides the molecular weight distribution of a material. GPC is also sometimes known as size exclusion chromatography (SEC). This technique is often used for the analysis of polymers for their both $M_n$ and $M_w$.

These commercially available and exemplary polyethyleneimines are soluble in water and available as anhydrous polyethyleneimines and/or modified polyethyleneimines provided in aqueous solutions or methoxypropanol (as for Lupasol® PO 100).

PEI and its derivatives find many applications usually derived from its polycationic character. Because of the presence of amine groups, PEI can be protonated with acids to form a PEI salt from the surrounding medium resulting in a product that is partially or fully ionized depending on pH. For example, about 73% of PEI is protonated at pH 2, about 50% of PEI is protonated at pH 4, about 33% of PEI is protonated at pH 5, about 25% of PEI is protonated at pH 8 and about 4% of PEI is protonated at pH 10. In general, PEIs can be purchased as their protonated or unprotonated form with and without water. The commercial PEIs at pH 13 have a charge (cationic) density of about 16-17 meq/g (milliequivalents per gram).

The counterion of each protonated nitrogen center is balanced with an anion of an acid obtained during neutralization. Examples of protonated PEI salts include, but are not limited to, PEI-hydrochloride salt, PEI-sulfuric acid salt, PEI-nitric acid salt, PEI-acetic acid salt PEI fatty acid salt and the like. In fact, any acid can be used to protonate PEIs resulting in the formation of the corresponding PEI salt compound.

Suitable polyethyleneimine useful in the present disclosure may contain a mixture of primary, secondary, and tertiary amine substituents or mixture of different average molecular weights. The mixture of primary, secondary, and tertiary amine substituents may be in any ratio, including for example in the ratio of about 1:1:1 to about 1:2:1 with branching every 3 to 3.5 nitrogen atoms along a chain segment. Alternatively, suitable polyethyleneimine compounds may be primarily one of primary, secondary or tertiary amine substituents.

The polyamine that can be used to make the multiple charged cationic or anionic compounds disclosed herein can have a wide range of its average molecular weight. Different multiple charged cationic or anionic compounds with their characteristic average molecular weights can be produced by selecting different starting small molecule polyamines, polymeric PEIs, or mixture thereof. Controlling the size of polyamines or PEI and extent of modification by the α,β-unsaturated compound and epoxide, one can produce the multiple charged cationic or anionic compounds with a similar average molecular weight and multiple cationic charges or multiple anionic charges. Because of this character, one can produce and use different multiple charged cationic or anionic compounds for a wider range of applications that are using unmodified polyamine or PEIs.

Specifically, the polyamines that can be used to make the modified polyamines disclosed here have an average molecular weight ($M_w$) of about 60-200, about 100-400, about 100-600, about 600-5,000, about 600-800, about 800-2,000, about 800-5,000, about 100-2,000,000, about 100-25,000, about 600-25,000, about 800-25,000, about 600-750,000, about 800-750,000, about 25,000-750,000, about 750,000-2,000,000, about 100, about 200, about 300, about 400, about 500, about 600, about 700, about 800, about 1,000, about 1,500, about 2,000, about 3,000, about 5,000, about 8,000, about 10,000, about 15,000, about 20,000, about 50,000, about 100,000, about 250,000, about 500,000, about 1,000,000, about 2,000,000, or any value there between.

In one aspect, disclosed herein is a multiple charge compound having one of the generic formula of $NA_2$-$[R^{10'}]_n$-$NA_2$, $(RNA)_n$-$RNA_2$, $NA_2$-$(RNA)_n$-$RNA_2$, or $NA_2$-$(RN(R'))_n$-$RNA_2$, wherein $R^{10'}$ is a linear or branched, unsubstituted or substituted $C_4$-$C_{10}$ alkylene group, or combination thereof; R is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkylene group, or combination thereof; R' is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkyl group, $RNA_2$, $RNARNA_2$, or $RN(RNA_2)_2$; n can be from 2 to 1,000,000; A is a combination of H,

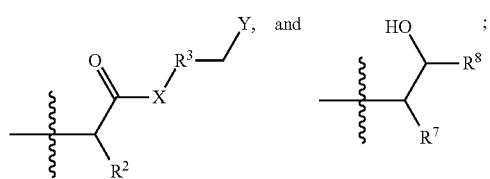

or a combination of H,

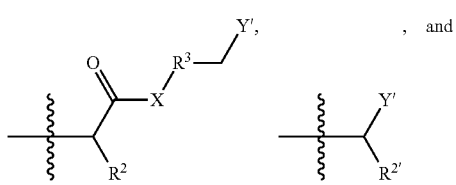

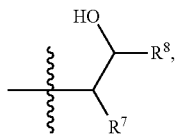

wherein X is NH or O; $R^2$ is H, $CH_3$, or an unsubstituted, linear or branched $C_2$-$C_{10}$ alkyl, alkenyl, or alkynyl group; $R^{2'}$ is H, $CH_3$, or an unsubstituted or substituted, linear or branched $C_1$-$C_{10}$ alkyl, alkenyl, alkynyl group, —COOH, —$CH_2COOH$, Y', or —$(CH_2)_m$—Y'; m is an integer of 2 to 4; $R^3$ is absent or an unsubstituted, linear or branched $C_1$-$C_{30}$ alkylene group; Y is —$NR_4R_5R_6^{(+)}$; Y' is —COOH, —$SO_3H$, —$PO_3H$, —$OSO_3H$, —$OPO_3H$, or a salt thereof; $R^4$, $R^5$, and $R^6$ are independently a $C_1$-$C_{10}$ alkyl group; $R^7$ is H or alkyl; and $R^8$ is alkyl, or —$(CH_2)_k$-O-alkyl, wherein k is an integer of 1-30; wherein the compound is a multiple charged cationic compound having 1, 2, 3, or more

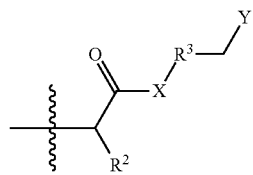

groups and at least one

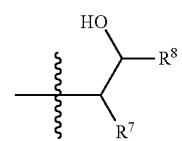

group or a multiple charged anionic compound having 1, 2, 3, or more

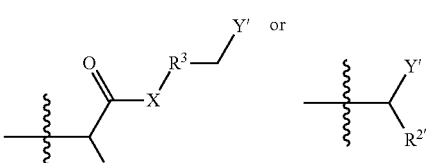

groups, and at least one

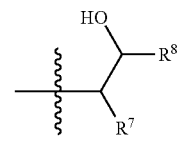

group.

In some embodiments, A is

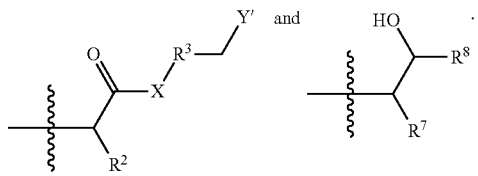

In some other embodiments, A is

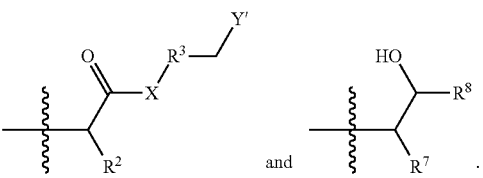

In yet some other embodiments, A is

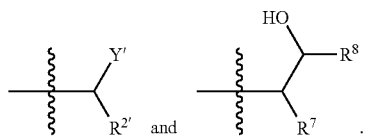

In some embodiments, the multiple charge compound is $NA_2$-$[R^{10'}]_n$-$NA_2$. In some other embodiments, the multiple charge compound is $(RNA)_n$-$RNA_2$. In yet some other embodiments, the multiple charge compound is $NA_2$-$(RNA)_n$-$RNA_2$. In some other embodiments, the multiple charge compound is $NA_2$-$(RN(R'))_n$-$RNA_2$.

In some embodiments, $R^7$ is H. In some other embodiments, $R^7$ is a $C_1$-$C_4$ alkyl group. In yet some other embodiments, $R^8$ is a $C_{12}$-$C_{20}$ alkyl group.

In another aspect, disclosed herein is a multiple charged compound derived from a polyamine through its reactions with an activated olefin and an epoxide, wherein the activated olefin has one of the following formulas;

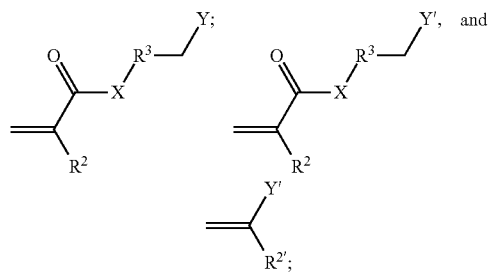

and the epoxide is

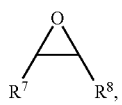

wherein X is NH or O; $R^2$ is H, $CH_3$, or an unsubstituted, linear or branched $C_2$-$C_{10}$ alkyl, alkenyl, or alkynyl group; $R^{2'}$ is H, $CH_3$, or an unsubstituted or substituted, linear or branched $C_1$-$C_{10}$ alkyl, alkenyl, alkynyl group, —COOH, —$CH_2COOH$, Y', or —$(CH_2)_m$—Y'; m is an integer of 2 to 4; $R^3$ is absent or an unsubstituted, linear or branched $C_1$-$C_{30}$ alkylene group; Y is —$NR_4R_5R_6^{(+)}$; Y' is —COOH, —$SO_3H$, —$PO_3H$, —$OSO_3H$, —$OPO_3H$, or a salt thereof; $R^4$, $R^5$, and $R^6$ are independently a $C_1$-$C_{10}$ alkyl group; $R^7$ is H or alkyl; and $R^8$ is alkyl, or —$(CH_2)_k$—O-alkyl, wherein k is an integer of 1-30; wherein the polyamine and activated olefin undergo aza Michael Addition reaction and the polyamine and epoxide undergo ring opening reaction; wherein the compound is a multiple charged cationic compound having 1, 2, 3, or more positive charges from the activated olefin and at least one nonionic group from the epoxide or a multiple charged anionic compound having 1, 2, 3, or more negative charges from the activated olefin and at least one nonionic group from the epoxide.

The multiple charge cationic or anionic compounds disclosed here are derived from a polyamine as a result of its aza-Michael addition with an activated olefin, such as α, β-unsaturated carbonyl compound, having an ionic group and its ring opening reaction with an epoxide.

Figure 2:
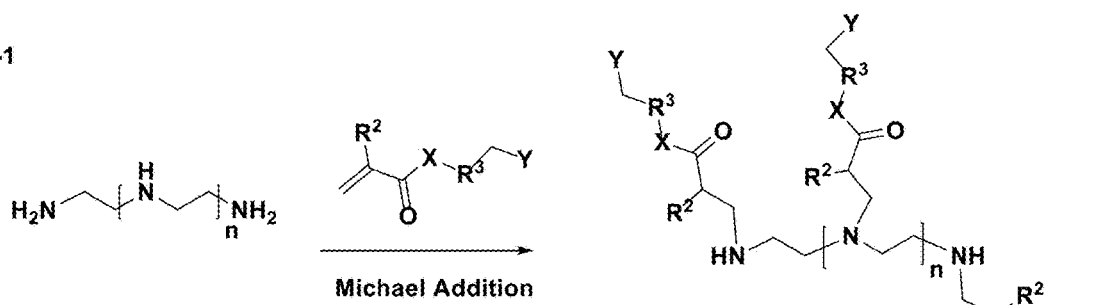
FIG. 2 shows an exemplary alternate generic reaction scheme to produce a multiple charged cationic compound first by an aza-Michael addition reaction between a linear polyethyleneimine and $\alpha,\beta$-unsaturated carbonyl compound and then a ring-opening reaction with an epoxide.
Figure 2:
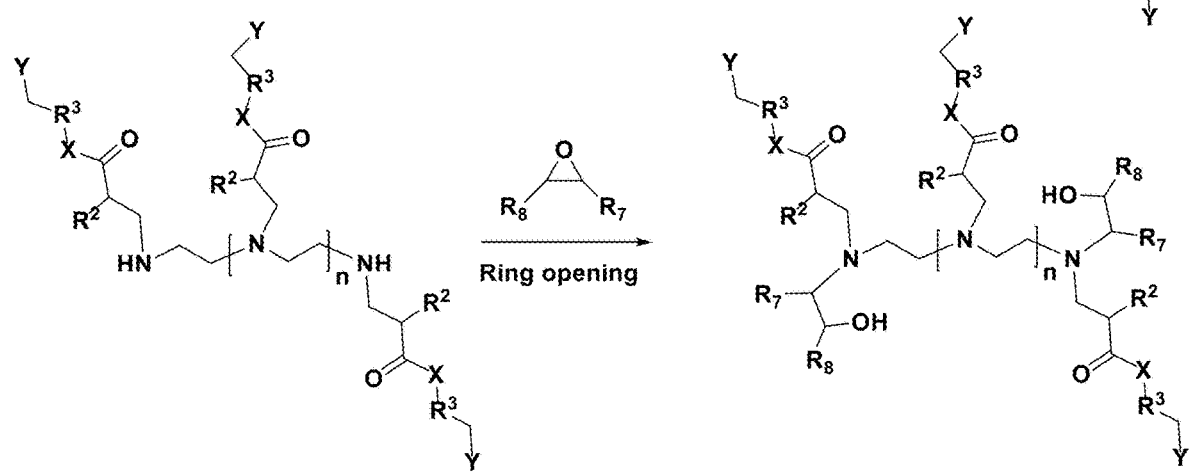
Figure 3:
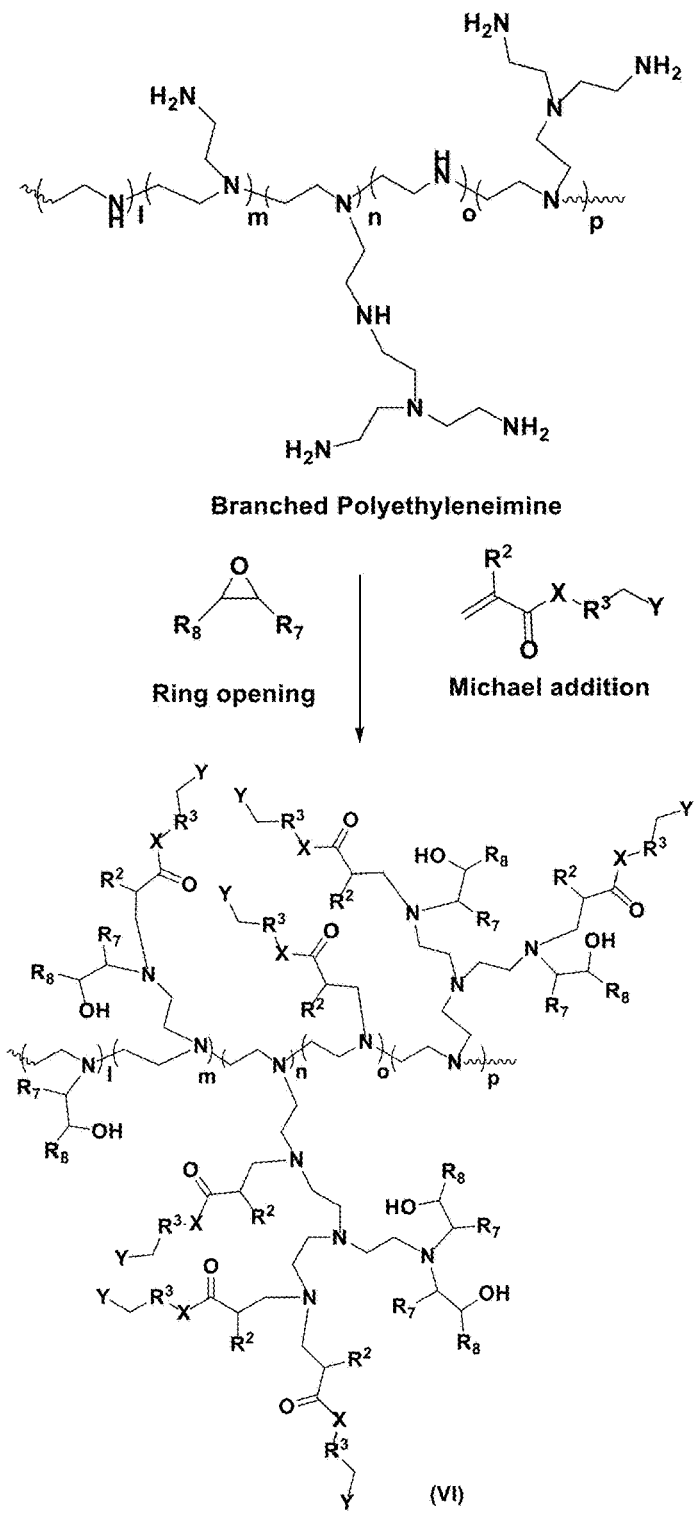
FIG. 3 shows an exemplary generic reaction scheme to produce a multiple charged cationic compound by reacting a branched polyethyleneimine with both an epoxide and a, $\beta$-unsaturated carbonyl compound through a ring-opening reaction and aza-Michael addition reaction, respectively.

The two reactions of a polyamine leading to the disclosed compound can be sequential or simultaneous, e.g., in three different ways as shown in FIG. 1, FIG. 2, and FIG. 3, which illustrates the generic schemes for the structures of and the reactions leading to the disclosed multiple charged cationic or anionic compounds.

FIG. 1 shows an exemplary generic reaction scheme to produce a multiple charged cationic compound first by a ring-opening reaction between a liner polyethyleneimine and epoxide and then an aza-Michael addition reaction with an activated olefin, e.g., an α, β-unsaturated carbonyl compound having a cationic group. FIG. 2 shows an exemplary alternate generic reaction scheme to produce a multiple charged cationic compound first by an aza-Michael addition reaction between a linear polyethyleneimine and α,β-unsaturated carbonyl compound and then a ring-opening reaction with an epoxide. FIG. 3 shows an exemplary generic reaction scheme to produce a multiple charged cationic compound by reacting a branched polyethyleneimine with both an epoxide and α,β-unsaturated carbonyl compound through a ring-opening reaction and aza-Michael addition reaction, respectively.

In FIG. 1, FIG. 2, and FIG. 3, k, l, m, n, o, or p is an integer of 1-100; X is NH or O; $R^2$ is H, $CH_3$, or an unsubstituted, linear or branched $C_2$-$C_{10}$ alkyl group; $R^3$ is absent or an unsubstituted, linear or branched $C_1$-$C_{30}$ alkylene group; Y is —$NR^4R^5R^{6(+)}$ or a salt thereof; $R^4$, $R^5$, and $R^6$ are independently $C_1$-$C_{10}$ alkyl group or benzyl group; $R^7$ is H or alkyl; and $R^8$ is alkyl, or —$(CH_2)_k$—O-alkyl, wherein k is an integer of 1-30.

The structures V and VI in FIG. 1, FIG. 2, and FIG. 3 are depiction of generalized reaction products. In structures V and VI, all the secondary and primary amine groups in the polyethyleneimine react with epoxides and α,β-unsaturated carbonyl compounds so that no secondary amine groups remain. It is possible that in the disclosed multiple charged ionic compounds, some secondary or primary amine groups do not react completely with either the epoxide or activated olefin and remain as primary or secondary amine groups in the multiple charged ionic compound or its salt.

In some embodiments, $R^7$ is H. In some other embodiments, $R^7$ is $CH_3$. In yet some other embodiments, $R^7$ is a $C_2$-$C_4$ alkyl.

In some embodiments; $R^8$ is a $C_1$-$C_{30}$ alkyl. In some other embodiments, $R^8$ is $C_8$-$C_4$ alkyl. In yet some other embodiments, $R^8$ is a $C_8$-$C_{20}$ alkyl.

In some embodiments, $R^8$ is —$(CH_2)_k$—O-alkyl, wherein k is an integer of 1-30 and the alkyl group is $C_1$-$C_{30}$ alkyl group.

In some embodiments, the polyamine is $NH_2$—$[R^{10'}]_n$-$NH_2$, $(RNH)_n$—$RNH_2$, $H_2N$—$(RNH)_n$—$RNH_2$, or $H_2N$—$(RN(R'))_n$—$RNH_2$, wherein $R^{10'}$ is a linear or branched, unsubstituted or substituted $C_2$-$C_{10}$ alkylene group, or combination thereof; R is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkylene group, or combination thereof; R' is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkyl group, $RNH_2$, $RNHRNH_2$, or $RN(RNH_2)_2$; and n can be from 2 to 1,000,000. The monomer in a polyamine, e.g., the R or R' group, can be the same or different. In this disclosure, a polyamine refers to both small molecule polyamine when n is from 1 to 9 and polymeric polyamine when n is from 10 to 1,000,000.

In other words, the multiple charged ionic compound can have a formula of $NA_2-[R^{10'}]_n-NA_2$, $(RNA)_n-RNA_2$, $NA_2-(RNA)_n-RNA_2$, or $NA_2-(RN(R'))_n-RNA_2$, or the like, wherein $R^{10'}$ is a linear or branched, unsubstituted or substituted $C_4-C_{10}$ alkylene group; R is $—CH_2—$, $—CH_2CH_2—$, $—CH_2CH_2CH_2—$, $—CH(CH_3)CH_2—$, a linear or branched, unsubstituted or substituted $C_4-C_{10}$ alkylene group, or combination thereof; R' is $—CH_2—$, $—CH_2CH_2—$, $—CH_2CH_2CH_2—$, $—CH(CH_3)CH_2—$, a linear or branched, unsubstituted or substituted $C_4-C_{10}$ alkyl group, $RNA_2$, $RNARNA_2$, or $RN(RNA_2)_2$; n can be from 2 to 1,000,000; A is a combination of H,

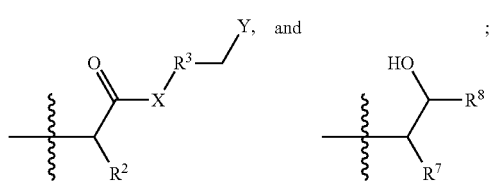

or a combination of H,

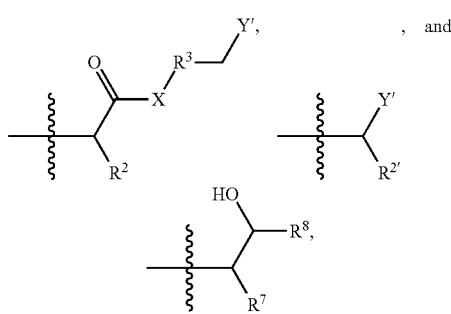

wherein X is NH or O; $R^2$ is H, $CH_3$, or an unsubstituted, linear or branched $C_2-C_{10}$ alkyl, alkenyl, or alkynyl group; $R^{2'}$ is H, $CH_3$, or an unsubstituted or substituted, linear or branched $C_1-C_{10}$ alkyl, alkenyl, alkynyl group, $—COOH$, $—CH_2COOH$, Y', or $—(CH_2)_m—Y'$; m is an integer of 2 to 4; $R^3$ is absent or an unsubstituted, linear or branched $C_1-C_{30}$ alkylene group; Y is $—NR_4R_5R_6^{(+)}$; Y' is $—COOH$, $—SO_3H$, $—PO_3H$, $—OSO_3H$, $—OPO_3H$, or a salt thereof; $R^4$, $R^5$, and $R^6$ are independently a $C_1-C_{10}$ alkyl group; $R^7$ is H or alkyl; and $R^8$ is alkyl, or $—(CH_2)_k—O-alkyl$, wherein k is an integer of 1-30; wherein the compound is a multiple charged cationic compound having 1, 2, 3, or more positive charges from the activated olefin and at least one nonionic group from the epoxide or multiple charged anionic compound having 1, 2, 3, or more negative charges from the activated olefin and at least one nonionic group from the epoxide.

In some embodiments, A is positively charged

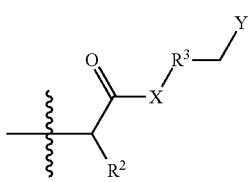

and nonionic

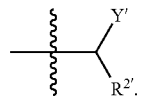

In some other embodiments, A is negatively charged

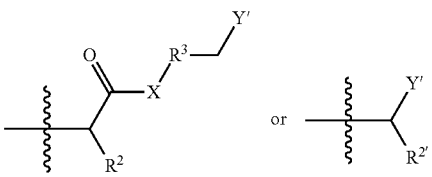

and nonionic

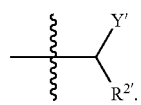

In some embodiments, at least two of the primary $NH_2$ protons were replaced by

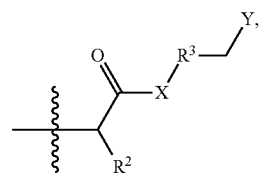

at least one of the primary $NH_2$ or secondary NH were replaced by

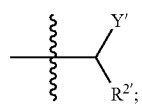

and the rest of primary $NH_2$ protons remains. In some embodiments, at least two of the primary $NH_2$ protons were replaced by

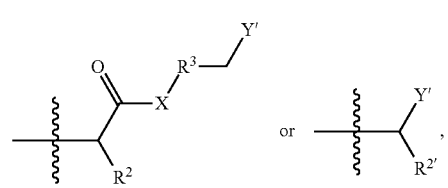

at least one of the primary $NH_2$ or secondary NH is replaced by

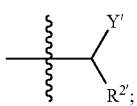

and the rest of primary NH$_2$ protons remains.

In some other embodiments, all of the primary NH$_2$ protons are replaced by

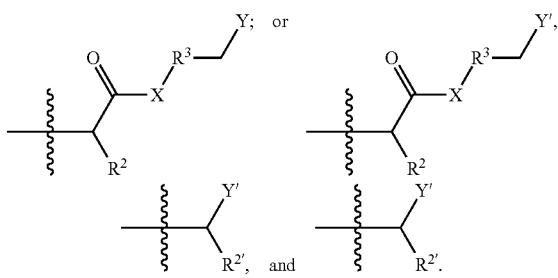

In some embodiments, some of primary NH$_2$ and secondary NH proton are replaced by

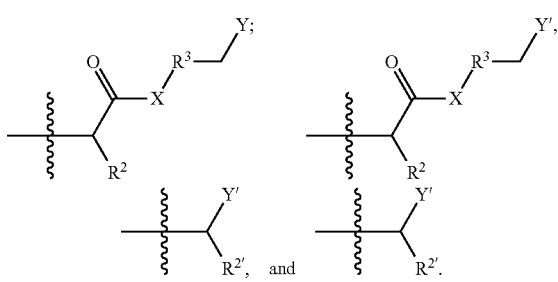

In some embodiments, all of primary NH$_2$ and some of secondary NH proton are replaced by

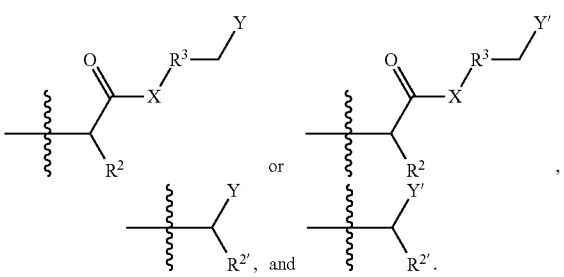

Nevertheless, the compounds disclosed herein are multiple charged cationic compounds having 1, 2, 3, or more

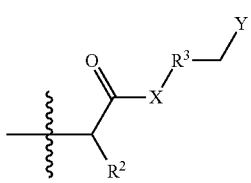

groups and at least one

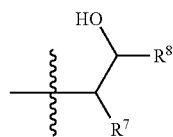

group or multiple charged anionic compounds having 1, 2, 3, or more

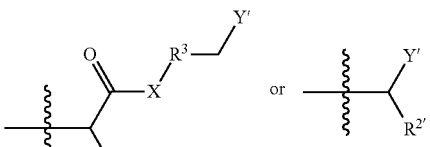

groups, and at least one

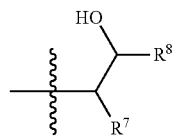

group.

In some embodiments, R$^2$ is H. In some embodiments, R$^2$ is CH$_3$. In yet some other embodiments, R$^2$ is CH$_3$CH$_3$, CH$_2$CH$_2$CH$_3$, or CH(CH$_3$)$_2$.

In some embodiments, Y is —NR$_4$R$_5$R$_6$$^{(+)}$. In some other embodiments, Y is —NR$_4$R$_5$R$_6$$^{(+)}$, and R$^4$, R$^5$, and R$^6$ are independently CH$_3$. In yet some other embodiments, Y is —NR$_4$R$_5$R$_6$$^{(+)}$, and R$^4$ and R$^5$, independently CH$_3$, and R$^6$ is a C$_6$-C$_{12}$ aromatic alkyl. In some other embodiments, Y is —NR$_4$R$_5$R$_6$$^{(+)}$, and R$^4$ and R$^5$, independently CH$_3$, and R$^6$ is —CH$_2$—C$_6$H$_6$.

In some embodiments, Y is —NR$_4$R$_5$R$_6$$^{(+)}$ and the counter ion for Y any negative charged ion or species. In some other embodiments, the counter ion for Y is selected from the group consisting of chloride, bromide, fluoride, iodide, acetate, aluminate, cyanate, cyanide, dihydrogen phosphate, dihydrogen phosphite, formate, carbonate, hydrogen carbonate, hydrogen oxalate, hydrogen sulfate, hydroxide, nitrate, nitrite, thiocyanate, and a combination thereof.

In some embodiments, Y' is —COOH or salt thereof. In some other embodiments, Y' is —SO$_3$H, —OSO$_3$H, or salt thereof. In yet some other embodiments, Y' is —PO$_3$H, —OPO$_3$H, or salt thereof.

In some embodiments, when Y is an anionic group, the counter position ions for the negative charge is Li$^+$, Na$^+$, K$^+$, NH$_3^+$, a quaternary ammonium, or the like.

In some embodiments, R$^3$ is CH$_2$. In some other embodiments, R$^3$ is CH$_2$CH$_2$. In other embodiments, R$^3$ is C(CH$_3$)$_2$. In yet some other embodiments, R$^3$ is an unsubstituted, linear, and saturated C$_1$-C$_{30}$ alkylene group. In some embodiments, R$^3$ is an unsubstituted, linear, and unsaturated C$_1$-C$_{30}$ alkylene group.

In some embodiments, R$^3$ is a linear C$_8$-C$_{18}$ alkyl, alkenyl, or alkynyl group. In some other embodiments, R$^3$ is a branched C$_8$-C$_{20}$ alkyl, alkenyl, or alkynyl group.

In some embodiments, the polyamine is a linear, branched, or dendrimer polyamine with a general formula of —[RNH]$_n$—, wherein R is —CH$_2$CH$_2$—, —CH$_2$CH$_2$CH$_2$—, —CH(CH$_3$)CH$_2$—, a linear or branched, unsubstituted or substituted C$_4$-C$_{10}$ alkylene group, or combination thereof and n is an integer of 3, 4, 5, 6, 7-9, or from 10 to 1,000,000.

In some embodiments, the polyamine is a linear, branched, or dendrimer polyamine with a general formula of (RNH)$_n$—RNH$_2$, wherein R is —CH$_2$—, —CH$_2$CH$_2$—, —CH$_2$CH$_2$CH$_2$—, —CH(CH$_3$)CH$_2$—, a linear or branched, unsubstituted or substituted C$_4$-C$_{10}$ alkylene group, or combination thereof and n can be from 2 to 1,000,000. In some embodiments, R is the same in each monomer. In some other embodiments, R can be different from one monomer to another monomer.

In some other embodiments, the polyamine is a linear, branched, or dendrimer polyamine with a general formula of H$_2$N—(RNH)$_n$—RNH$_2$, wherein R is —CH$_2$—, —CH$_2$CH$_2$—, —CH$_2$CH$_2$CH$_2$—, —CH(CH$_3$)CH$_2$—, a linear or branched, unsubstituted or substituted C$_4$-C$_{10}$ alkylene group, or combination thereof and n can be from 2 to 1,000,000. In some embodiments, R is the same in each monomer. In some other embodiments, R can be different from one monomer to another monomer.

In yet some other embodiments, the polyamine is a linear, branched, or dendrimer polyamine with a general formula of H$_2$N—(RN(R')$_n$—RNH$_2$, wherein R is —CH$_2$—, —CH$_2$CH$_2$—, —CH$_2$CH$_2$CH$_2$—, —CH(CH$_3$)CH$_2$—, a linear or branched, unsubstituted or substituted C$_4$-C$_{10}$ alkylene group, or combination thereof; R' is —CH$_2$—, —CH$_2$CH$_2$—, —CH$_2$CH$_2$CH$_2$—, —CH(CH$_3$)CH$_2$—, a linear or branched, unsubstituted or substituted C$_4$-C$_{10}$ alkyl group, RNH$_2$, RNHRNH$_2$, or RN(RNH$_2$)$_2$; and n can be from 2 to 1,000,000. In some embodiments, R or R' is the same in each monomer. In some other embodiments, R or R' can be different from one monomer to another monomer.

In some embodiments, the polyamine is one with a general formula of NH$_2$—[R$^{10'}$]$_n$-NH$_2$, wherein R$^{10'}$ is a linear or branched, unsubstituted or substituted C$_4$-C$_{10}$ alkylene group, or combination thereof and n is an integer of 3, 4, 5, 6, 7-9, or 10 to 1,000,000. In some embodiments, the polyamine is one or more of polyamines under JEFFAMINE® by Huntsman.

In some embodiments, the polyamine comprises an alkyleneamine, the alkyleneamine comprising ethylenediamine, diethylenetriamine, triethylenetetramine, tetraethylenepentamine, pentaethylenehexamine, hexaethyleneheptamine, polyethyleneimine, tris(2-aminoethyl)amine, or a mixture thereof.

In some other embodiments, the polyamine is a mixture of monoamine, diamine, and triamine with a polyether backbone or with a polyether backbone based on propylene oxide (PO), ethylene oxide (EO), or a mixture of both oxides In some embodiments, the polyamine is an unmodified polyamine. In some other embodiments, the polyamine is a modified polyamine.

In yet some embodiments, the polyamine is an ethoxylated polyamine, propylated polyamine, polyamine with polyquat, polyamine with polyglycerol, or combination thereof.

In yet some other embodiments, the polyamine is a linear, branched, or dendrimer polyethyleneimine. In some other embodiments, the polyamine comprises only primary and secondary amine groups. In some embodiments, the polyamine comprises only primary, secondary, and tertiary amine groups. In some other embodiments, the polyamine comprises only primary and tertiary amine groups.

In some embodiments, the polyamine is a single compound. In some other embodiments, the polyamine is a mixture of two or more different polyamines, wherein the different polyamines have different molecular weight, different structure, or both.

In some embodiments, the polyamine has an average molecular weight ($M_w$) of from about 60 to about 2,000,000 Da. In some other embodiments, the polyamine has an average molecular weight ($M_w$) of from about 60 to about 5,000 Da. In yet some other embodiments, the polyamine has an average molecular weight ($M_w$) of from about 60 to about 25,000 Da.

In some embodiments, the polyamine has an average molecular weight ($M_w$) of about 60-200, about 100-400, about 100-600, about 600-5,000, about 600-800, about 800-2,000, about 800-5,000, about 100-2,000,000, about 100-25,000, about 600-25,000, about 800-25,000, about 600-750,000, about 800-750,000, about 25,000-750,000, about 750,000-2,000,000, about 100, about 200, about 300, about 400, about 500, about 600, about 700, about 800, about 1,000, about 1,500, about 2,000, about 3,000, about 5,000, about 8,000, about 10,000, about 15,000, about 20,000, about 50,000, about 100,000, about 250,000, about 500,000, about 1,000,000, about 2,000,000, or any value there between.

In some embodiments, the polyamine is diamine or triamine having an average molecular weight ($M_w$) of from about 130 to about 4,000.

In some embodiments, the compound is a mixture derived from a linear polyethyleneimine and (3-Acrylamidopropyl)trimethylammonium chloride (APTAC). In some other embodiments, the compound is a mixture derived from a linear polyethyleneimine and [3-(Methacryloylamino)propyl]trimethylammonium chloride (MAPTAC).

In some other embodiments, the multiple charged cationic compound is a mixture derived from a branched polyethyleneimine and 3-Acrylamidopropyl)trimethylammonium chloride (APTAC). In some other embodiments, the compound is a mixture derived from a linear polyethyleneimine and [3-(Methacryloylamino)propyl]trimethylammonium chloride (MAPTAC).

In some embodiments, the activated olefin is (3-Acrylamidopropyl)trimethylammonium chloride (APTAC), [3-(Methacryloylamino)propyl]trimethylammonium chloride (MAPTAC), 2-(acryloyloxy)-N,N,N-trimethylethanaminium chloride (DMAEA-MCQ), N,N-dimethylaminoethyl acrylate benzyl chloride quaternary salt (DMAEA-BCQ), or 2-(methacryloyloxy)-N,N,N-trimethylethan-1-aminium methyl sulfate (DMAEA-MSQ).

In some other embodiments, the activated olefin is (3-Acrylamidopropyl)trimethylammonium chloride (APTAC), [3-(Methacryloylamino)propyl]trimethylammonium chloride (MAPTAC), or mixture thereof.

In some other embodiments, the activated olefin is 2-(acryloyloxy)-N,N,N-trimethylethanaminium chloride (DMAEA-MCQ), N,N-dimethylaminoethyl acrylate benzyl chloride quaternary salt (DMAEA-BCQ), 2-(methacryloyloxy)-N,N,N-trimethylethan-1-aminium methyl sulfate (DMAEA-MSQ), or a mixture thereof.

In some embodiments, the activated olefin is an acrylic acid, methacrylic acid, 2-acrylamido-2-methylpropane sulfonic acid, itaconic acid, maleic acid, 3-(allyloxy)-2-hydroxypropane-1-sulfonate, or their salts or mixture thereof.

In some other embodiments, the activated olefin is vinylsulfonic acid, vinylphosphonic acid, or mixture thereof.

In some embodiments, the epoxide is an alkylglyicdal ether, hexylglycidal ether, octylglycidal ether, dodecyglycidal ether, a 1,2-epoxyalkane, 1,2-epoxytertadecane, 1,2-epoxydodecane, or 1,2-epoxyoctane, or mixture thereof. In some other embodiments, the epoxide is an alkylglyicdal ether or 1,2-epoxyalkane. In yet some other embodiments, the epoxide is hexylglycidal ether, octylglycidal ether, dodecyglycidal ether, or mixture thereof. In some other embodiments, the epoxide is 1,2-epoxytertadecane, 1,2-epoxydodecane, or 1,2-epoxyoctane, or mixture thereof.

In yet some other embodiments, when the activated olefin contains anionic group that can bear negative charge at an alkaline pH, the counter positive ions for the negative charges include, but are not limited to, alkali metal ions, $Li^+$, $Na^+$, $K^+$, $NH_4^+$, a quaternary ammonium ion, etc.

In some embodiments, the compound is a product from an epoxide, (3-Acrylamidopropyl) trimethylammonium chloride (APTAC) and a polyethylenimine with an average molecular weight ($M_w$) of about 1,300, a polyethylenimine with an average molecular weight ($M_w$) of about 5,000, a polyethylenimine with an average molecular weight ($M_w$) of about 25,000, or a polyethylenimine with an average molecular weight ($M_w$) of about 750,000, respectively.

It should be understood that when n is greater than 2, the compound can be a mixture of more than two cationic compounds, which differ from each other by the exact locations of NH replacements.

In some embodiments, the multiple charged cationic or anionic compound has an average molecular weight ($M_w$) of from about 100 to about 2,000,000 Da. In some other embodiments, the multiple charged cationic or anionic compound has an average molecular weight ($M_w$) of from about 100 to about 50,000 Da. In yet some other embodiments, the multiple charged cationic or anionic compound has an average molecular weight ($M_w$) of from about 100 Da to about 600 Da, from about 100 Da to about 1,000 Da, from about 100 Da to about 1,400 Da, from about 100 Da to about 3,000 Da, from about 100 Da to about 5,500 Da, or from about 100 Da to about 10,000 Da, from about 100 Da to about 20,000 Da, from about 100 Da to about 30,000 Da, or from about 100 Da to about 40,000 Da.

In some embodiments, the multiple charged cationic compound has at least 2, at least 3, at least 4, at least 5, at least 6, at least 7, at least 8, at least 9, or at least 10 positive charges. In some other embodiments, the compound has from 10 to 1,000 positive charges, or any value there between positive charges.

In some embodiments, the multiple charged cationic compound has at least 2, at least 3, at least 4, at least 5, at least 6, at least 7, at least 8, at least 9, or at least 10 negative charges. In some other embodiments, the compound has from 10 to 1,000 positive charges, or any value there between negative charges.

In some embodiments, the compound or the modified compound is soluble or dispersible in water.

Aza-Michael Addition Reaction and Ring Opening Reaction of Epoxide

The multiple charged cationic or anionic compounds disclosed herein are derived from an aza-Michael Addition Reaction between a polyamine and Michael acceptor such as an activated olefin or α,β-unsaturated carbonyl compound containing a hydrophilic (ionic) group and from a ring opening reaction between a polyamine and epoxide. The aza Michael Addition Reaction and the ring opening reaction can happen sequentially or simultaneously. In some embodiments, the reaction products of the aza-Michael Addition reaction are further derived with a ring opening reaction of an epoxide. Alternatively, the multiple charged cationic or anionic compounds disclosed herein are derived from a ring opening reaction between a polyamine and epoxide and the products of the ring opening reaction then react with Michael acceptor such as an activated olefin or α,β-unsaturated carbonyl compound containing a hydrophilic (ionic) group through an aza-Michael Addition Reaction between the product.

An aliphatic amine group may undergo an aza-Michael Addition reaction when in contact with an unsaturated hydrocarbon moiety (e.g., carbon-carbon double bond) that is in proximity of an electron withdrawing group such as carbonyl, cyano, or nitro group. Specifically, the Michael addition is a reaction between nucleophiles and activated olefin and alkyne functionalities, wherein the nucleophile adds across a carbon-carbon multiple bond that is adjacent to an electron withdrawing and resonance stabilizing activating group, such as a carbonyl group. The Michael addition nucleophile is known as the "Michael donor", the activated electrophilic olefin is known as the "Michael acceptor", and reaction product of the two components is known as the "Michael adduct." Examples of Michael donors include, but are not restricted to, amines, thiols, phosphines, carbanions, and alkoxides. Examples of Michael acceptors include, but are not restricted to, acrylate esters, alkyl methacrylates, acrylonitrile, acrylamides, maleimides, cyanoacrylates and vinyl sulfones, vinyl ketones, nitro ethylenes, α,β-unsaturated aldehydes, vinyl phosphonates, acrylonitrile, vinyl pyridines, azo compounds, beta-keto acetylenes and acetylene esters.

As used herein, an "activated olefin" refers to a substituted alkene in which at least one of the double-bond carbon has a conjugated electron withdrawing group. Examples of activated olefins include, but not limited to, α,β-unsaturated carbonyl compounds (such as $CH_2$=CHCO—NH—$CH_3$, alkyl-CH=CH—CO-alkyl, $CH_2$=$CH_2$C(O)—O—$CH_3$), $CH_2$=CH—COOH, $CH_2$=CH($CH_3$)—COOH, $CH_2$=CH—$SO_3$H, and like.

Aza-Michael addition reaction can be catalyzed by a strong acid or base. In some cases, some ionic liquids can function both as reaction media and catalyst. The preferred catalyst for the Aza-Michael addition reaction to synthesize the disclosed compounds is a base. Exemplary base catalyst can be hydroxide and amines. Because the reaction to synthesize the disclosed compounds uses a polyamine, the polyamine itself can function as a catalyst for the reaction. In such embodiments, no additional catalyst is necessary, or an additional catalyst is optional. Other preferred catalysts include amidine and guanidine bases.

The use of solvent and/or diluent for the reaction is optional. When employed, a wide range of non-acidic solvents are suitable, such as, for example, water, ethers (e.g., tetrahydrofuran (THF)), aromatic hydrocarbons (e.g., toluene and xylene), alcohols (e.g., n-butanol), and the like. A wide range of solvents can be used for the reaction because the synthesis process is relatively insensitive to solvent. When solvent (or diluent) is employed, loading levels can range from as low as about 10 wt-% up to about 80 wt-% and higher. The solvent loading level can be about 0 wt-%, from about 1 wt-% to about 10 wt-%, from about 10 wt-% to about 20 wt-%, from about 20 wt-% to about 30 wt-%, from about 30 wt-% to about 40 wt-%, from about 40 wt-% to about 50 wt-%, from about 50 wt-% to about 60 wt-%, from about 60 wt-% to about 70 wt-%, from about 70 wt-% to about 80 wt-%, from about 1 wt-% to about 20 wt-%, from about 20 wt-% to about 40 wt-%, from about 40 wt-% to about 60 wt-%, from about 60 wt-% to about 80 wt-%, from about 40 wt-% to about 70 wt-%, about 5 wt-%, about 15 wt-%, about 25 wt-%, about 35 wt-%, about 45 wt-%, about 55 wt-%, about 65 wt-%, about 75 wt-%, or any value there between of the final reaction mixture.

Generally, the reaction can be carried out at a temperature over a wide range of temperatures. The reaction temperature can range from about 0° C. to about 150° C., more preferably from about 50° C. to about 80° C. The contacting temperature can be from about 10° C. to about 140° C., about 20° C. to about 130° C., about 30° C. to about 120° C., about 40° C. to about 110° C., about 50° C. to about 100° C., about 60° C. to about 90° C., about 70° C. to about 80° C., about 0° C. to about 20° C., about 20° C. to about 40° C., about 40° C. to about 60° C., about 60° C. to about 80° C., about 80° C. to about 100° C., about 100° C. to about 120° C., about 120° C. to about 150° C., about 5° C., about 25° C., about 45° C., about 65° C., about 85° C., about 105° C., about 125° C., about 145° C., or any value there between. The reaction temperature can be about the same from starting of the reaction to end of the reaction and can be changed from one temperature to another while the reaction is going on.

The reaction time for the synthesis of the compounds disclosed herein can vary widely, depending on such factors as the reaction temperature, the efficacy and amount of the catalyst, the presence or absence of diluent (solvent), and the like. The preferred reaction time can be from about 0.5 hours to about 48 hours, from about 1 hour to 40 hours, from about 2 hours to 38 hours, from about 4 hours to about 36 hours, from 6 hours to about 34 hours, from about 8 hours to about 32 hours, from about 10 hours to about 30 hours, from about 12 hours to about 28 hours, from about 14 hours to 26 hours, from about 16 hours to 24 hours, from about 18 hours to 20 hours, from about 1 hour to 8 hours, from 8 hours to 16 hours, from 8 hours to about 24 hours, about 2 hours, about 4 hours, about 6 hours, about 8 hours, about 10 hours, about 14 hours, about 16 hours, about 18 hours, about 24 hours, about 30 hours, about 36 hours, or any values there between.

The ring opening reaction of an epoxide with an amine is also known in the prior art. This ring opening reaction can be done at a temperature of from about −20° C. to about 200° C. and in the presence of a catalyst, base, or acid. In some embodiments, the ring opening reaction is done free of a catalyst, base, or acid. In some other embodiments, the ring opening reaction is at a temperature from about 100° C. to about 150° C.; a different temperature for the aza Michael Addition reaction; in the presence of a different catalyst, base, or acid.

Both aza Michael addition and ring opening reactions for synthesis of the compounds disclosed can be accomplished when one mole of the polyamine and specified moles (two or more moles) of the activated olefin, the epoxide, and the both, are mixed together for a sufficient of time at a temperature described above.

It was found that the Aza-Michael addition and ring opening reaction of an epoxide can be used to synthesize the disclosed compounds without having to use a higher temperature greater than 200° C. and high pressure greater than normal atmosphere pressure and with a high yield (greater than 98%).

The progression of both reactions can be typically monitored by ESI-MS and/or NMR spectroscopy for consumption of the monomer. The reaction products can be purified or separated by HPLC or other methods known by one skilled in the art. For reactions that proceeded to completion, the formed product can be separated by removal of solvent or by precipitation in a non-polar solvent that was the opposite of the reaction media. For the reactions in water, the formed product is precipitated from the aqueous reaction mixture. Higher pressure can speed-up the reaction. Typically, if the reaction is carried out at a room temperature with an appropriate catalyst, the reaction can have a product yield of more than 98%, in some embodiments within 16 hours.

Method of Making

In another aspect, disclosed here is a method of making a compound or its salt, wherein the method comprises contacting a polyamine with an epoxide of

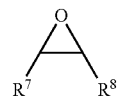

and an activated olefin (Michael acceptor) having an ionic group according to one of the following formulas

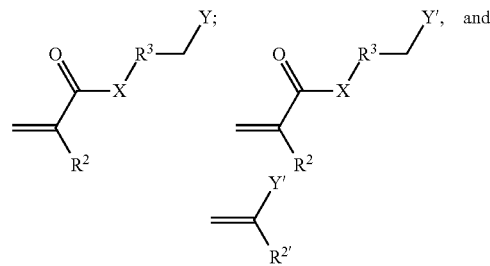

wherein X is NH or O; $R^2$ is H, $CH_3$, or an unsubstituted, linear or branched $C_2$-$C_{10}$ alkyl, alkenyl, or alkynyl group; $R^{2'}$ is H, $CH_3$, or an unsubstituted or substituted, linear or branched $C_1$-$C_{10}$ alkyl, alkenyl, alkynyl group, —COOH, —$CH_2$COOH, Y', or —$(CH_2)_m$—Y'; m is an integer of 2 to 4; $R^3$ is absent or an unsubstituted, linear or branched $C_1$-$C_{30}$ alkylene group; Y is —$NR_4R_5R_6^{(+)}$, Y' is —COOH, —$SO_3$H, —$PO_3$H, —$OSO_3$H, —$OPO_3$H, or a salt thereof; and $R^4$, $R^5$, and $R^6$ are independently a $C_1$-$C_{10}$ alkyl group; $R^7$ is H or alkyl; and $R^8$ is alkyl, or —$(CH_2)_k$—O-alkyl, wherein k is an integer of 1-30; wherein the polyamine and the activated olefin undergo aza-Michael addition reaction; the polyamine and the epoxide undergo a ring opening reaction; and wherein the compound is a multiple charged cationic compound having 1, 2, 3, or more positive charges from the activated olefin and at least one nonionic group from the epoxide or multiple charged anionic compound having 1, 2, 3, or more negative charges from the activated olefin and at least one nonionic group from the epoxide.

In some embodiments of the disclosed methods, the polyamine is a $NH_2$—$[R^{10'}]_n$—$NH_2$, $(RNH)_n$—$RNH_2$, $H_2N$—$(RNH)_n$—$RNH_2$, $H_2N$—$(RN(R'))_n$—$RNH_2$, or a mixture thereof, wherein $R^{iii}$ is a linear or branched, unsubstituted or substituted $C_2$-$C_{10}$ alkylene group, or combination thereof; R is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkylene group, or combination thereof; R' is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkyl group, $RNH_2$, $RNHRNH_2$, or $RN(RNH_2)_2$ and n can be from 2 to 1,000,000.

In some embodiments, the activated olefin is

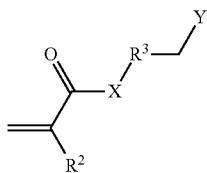

wherein X is NH or O; $R^2$ is H, $CH_3$, or an unsubstituted, linear or branched $C_2$-$C_{10}$ alkyl, alkenyl, or alkynyl group; $R^3$ is absent or an unsubstituted, linear or branched $C_1$-$C_{30}$ alkylene group; Y is —$NR_4R_5R_6^{(+)}$, and $R^4$, $R^5$, and $R^6$ are independently a $C_1$-$C_{10}$ alkyl group In some embodiments, the activated olefin activated olefin is (3-Acrylamidopropyl)trimethylammonium chloride (AP-TAC), [3-(methacryloylamino)propyl]trimethylammonium chloride (MAPTAC), 2-(acryloyloxy)-N,N,N-trimethylethanaminium chloride (DMAEA-MCQ), N,N-dimethylaminoethyl acrylate benzyl chloride quaternary salt (DMAEA-BCQ), 2-(methacryloyloxy)-N,N,N-trimethylethan-1-aminium methyl sulfate (DMAEA-MSQ), or a mixture thereof.

In some embodiments, Y is —$NR_4R_5R_6^{(+)}$ and the counter ion for Y any negative charged ion or species. In some other embodiments, the counter ion for Y is chloride, bromide, fluoride, iodide, acetate, aluminate, cyanate, cyanide, dihydrogen phosphate, dihydrogen phosphite, formate, carbonate, hydrogen carbonate, hydrogen oxalate, hydrogen sulfate, hydroxide, nitrate, nitrite, thiocyanate, or a combination thereof.

In some other embodiments of the disclosed methods, the activated olefin is

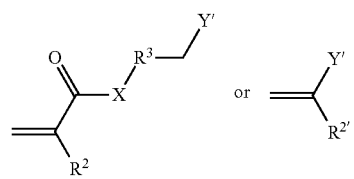

wherein X is NH or O; $R^2$ is H, $CH_3$, or an unsubstituted, linear or branched $C_2$-$C_{10}$ alkyl, alkenyl, or alkynyl group; $R^{2'}$ is H, $CH_3$, or an unsubstituted or substituted, linear or branched $C_1$-$C_{10}$ alkyl, alkenyl, alkynyl group, —COOH, —$CH_2COOH$, Y', or —$(CH_2)_m$—Y'; m is an integer of 2 to 4; $R^3$ is absent or an unsubstituted, linear or branched $C_1$-$C_{30}$ alkylene group; Y' is —COOH, —$SO_3H$, —$PO_3H$, —$OSO_3H$, —$OPO_3H$, or a salt thereof; and $R^4$, $R^5$, and $R^6$ are independently a $C_1$-$C_{10}$ alkyl group In some embodiments, the activated olefin is acrylic acid, methacrylic acid, itaconic acid, maleic acid, vinylsulfonic acid, vinylphosphonic acid, or mixture thereof.

In some other embodiments, the activated olefin is 2-acrylamido-2-methylpropane sulfonic acid (AMPS), 3-(allyloxy)-2-hydroxypropane-1-sulfonate, or mixture thereof.

In yet some other embodiments, when the activated olefin contains an anionic group that can bear negative charge at an alkaline pH, the counter positive ions for the negative charges include, but are not limited to, alkali metal ions, $Li^+$, $Na^+$, $K^+$, $NH_4^+$, a quaternary ammonium ion, etc.

In some embodiments, $R^7$ is H. In some other embodiments, $R^7$ is $CH_3$. In yet some other embodiments, $R^7$ is a $C_2$-$C_4$ alkyl.

In some embodiments; $R^8$ is a $C_1$-$C_{30}$ alkyl. In some other embodiments, $R^8$ is $C_8$-$C_4$ alkyl. In yet some other embodiments, $R^8$ is a $C_8$-$C_{20}$ alkyl.

In some embodiments, $R^8$ is —$(CH_2)_k$—O-alkyl, wherein k is an integer of 1-30 and the alkyl group is $C_1$-$C_{30}$ alkyl group.

In some embodiments, the epoxide is an alkylglyicdal ether, hexylglycidal ether, octylglycidal ether, dodecyglycidal ether, a 1,2-epoxyalkane, 1,2-epoxytertadecane, 1,2-epoxydodecane, or 1,2-epoxyoctane, or mixture thereof. In some other embodiments, the epoxide is an alkylglyicdal ether or 1,2-epoxyalkane. In yet some other embodiments, the epoxide is hexylglycidal ether, octylglycidal ether, dodecyglycidal ether, or mixture thereof. In some other embodiments, the epoxide is 1,2-epoxytertadecane, 1,2-epoxydodecane, or 1,2-epoxyoctane, or mixture thereof.

In some embodiments of the disclosed methods, the contacting step is done in the presence of a reaction solvent. The reaction solvent can be any inorganic or organic solvent commonly used in chemical synthesis. The reaction solvent used in the disclosed method can be introduced into the reaction between the polyamine and the activated olefin including a cationic or anionic group and between the polyamine and the epoxide by any way known by one skilled in the art. For example, the solvent can be added into the container or vessel for reaction before, at the same, with one or both reactants, or after the polyamine, the activated olefin, or both are added.

In some embodiments, the reaction solvent is water, methanol, ethanol, propanol, glycol, PEG, or a mixture thereof. In some other embodiments, the reaction solvent is water.

In some other embodiments of the disclosed methods, the contacting step is done in the presence of a catalyst, base, or acid. The catalyst, base, or acid can be introduced into the reaction between the polyamine and activated olefin by any way known by one skilled in the art.

In some embodiments, the contacting step is done without the presence of any additional base or alkalinity source. In some other embodiments, the contacting step is done in the presence of an alkalinity source. In some other embodiments, the contacting step is done in the presence of an organic base, such as alkanolamines. In yet some other embodiments, the contacting step is done in the presence of an alkali metal hydroxide, carbonate, imidazole/pyridine base, or combination thereof, such as NaOH, $Na_2CO_3$, aminoethyl pyridine, aminopropyl imidazole, or a combination thereof. In some other embodiments, the contacting step is done with the presence of benzyltrimethylammonium hydroxide. In some embodiments, the catalyst base is an amidine or guanidine base, or mixtures thereof. In some other embodiments, the catalyst is an ionic liquid, such as 1,8-diazabicyclo[5.4.0]-undec-7-en-8-ium acetate, for the reaction under a solvent free condition at room temperatures.

In yet some other embodiments of the disclosed methods, the contacting step is done in the presence of an acid. In some other embodiments, the contacting step is done in the presence of a catalyst. The catalyst can any one or more of the catalysts known for the Michael addition reaction by one skilled in the art.

In yet some other embodiments of the disclosed methods, the contacting step is done free of a catalyst, base, or acid. In some other embodiments, the contacting step is done free of an alkali metal hydroxide, carbonate, silicate, metasilicate, imidazole/pyridine-based base, or all thereof. In some embodiments, the contact step is done free of a base.

In some embodiments, the contacting step is a two-step process, first between the polyamine and the activated olefin and then between the product and the epoxide. In some other embodiments, the contacting step is a two-step process, first between the polyamine and the epoxide and the between the product and the activated olefin. In yet some other embodiments, the contacting step is a single step wherein contacting the polyamine with both the epoxide and activated olefin occurs. When the contacting step is a two-step process, the two steps can be done at two difference temperatures of from about −20° C. to about 200° C. In some embodiments, the contacting step with the activated olefin is done at a temperature from about 20° C. to about 120° C. In some other embodiments, the contacting step with the epoxide is done at the temperature from about 100° C. to about 150° C.

In yet another aspect, provided herein is an article, product, or composition that comprises one or more compounds disclosed herein.

In some embodiments, the article, product or composition further comprises a carrier solvent or a carrier. As used herein, a "carrier solvent" or carrier is a solvent or solvent system in which the disclosed compound can be distributed evenly and stable.

As used herein, "stable" means that compounds disclosed herein does not precipitate from or separated from the carrier solvent or other ingredients in the composition in about 1 hour, from about 1 hour to about 12 hours, about 12 hours, about 1 day, about 5 days, about 10 days, about 20 days, about 1 month, from about 1 month to about 1 year, or from about 1 year to about 2 year after the compounds disclosed herein and carrier solvent or any other ingredients are mixed homogenously.

In some other embodiments, the carrier is water, an organic solvent, or a mixture thereof. In some embodiments, the article, product, or composition further comprises an organic solvent. In some other embodiments, the article, product, or composition further comprises an organic solvent and water.

In some embodiments, the organic solvent is an alcohol, a hydrocarbon, a ketone, an ether, an alkylene glycol, a glycol ether, an amide, a nitrile, a sulfoxide, an ester, or any combination thereof. In some other embodiments, the organic solvent is an alcohol, an alkylene glycol, an alkyleneglycol alkyl ether, or a combination thereof. In yet some embodiments, the organic solvent is methanol, ethanol, propanol, isopropanol, butanol, isobutanol, monoethyleneglycol, ethyleneglycol monobutyl ether, or a combination thereof.

In some embodiments, the organic solvent is methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone.

In some embodiments, the article, product or composition can further comprise an additional surfactant. The additional surfactant is a nonionic, semi-nonionic, anionic, cationic, amphoteric, zwitterionic, Gemini, di-cationic, di-anionic surfactant, or combinations thereof.

In some embodiments, the articles, products, or compositions are solid. In some other embodiments, the articles, products, or compositions are liquid.

As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present disclosure may comprise, consist essentially of, or consist of the components and ingredients of the disclosed compositions or methods as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

EXAMPLES

Embodiments of the present disclosure are further defined in the following non-limiting Examples. These Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

Example 1

General Scheme to Synthesize Exemplary Compounds

Figure 4:
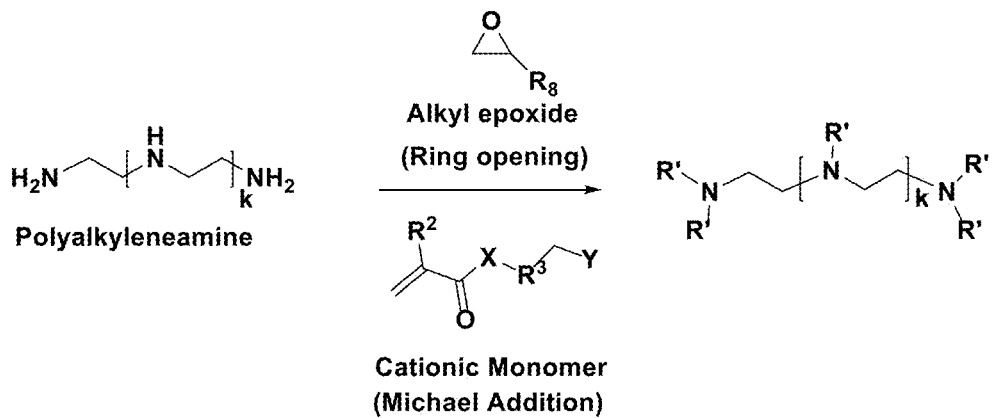
FIG. 4 shows a generic reaction scheme to produce a multiple charged cationic compound by reacting a linear polyethyleneimine with both an epoxide and $\alpha,\beta$-unsaturated carbonyl compound through a ring-opening reaction and aza-Michael addition reaction, respectively.
Figure 4:
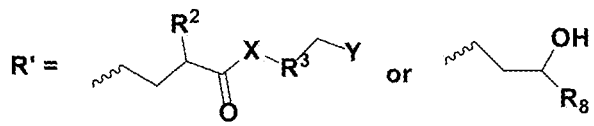

The generic synthesis reaction scheme for preparation of the multiple charged cationic or anionic compounds disclosed herein is FIG. 4. In this generic scheme, a linear polyethyleneimine is used as a representative for polyamines. Hydrogens on the nitrogen of the linear polyethyleneimine are replaced by both the cationic groups via aza Michael addition reactions and the hydrophobic groups via epoxide ring-opening reaction. Different compositions can be created by varying amounts of the ionic monomers and hydrophobic alkyl epoxide.

In FIG. 4, k is a integer of 1-100; X is NH or O; $R^2$ is H, $CH_3$, or an unsubstituted, linear or branched $C_2$-$C_{10}$ alkyl group; $R^3$ is absent or an unsubstituted, linear or branched $C_1$-$C_{30}$ alkylene group; Y is —$NR^4R^5R^{6(+)}$ or a salt thereof; $R^4$, $R^5$, and $R^6$ are independently $C_1$-$C_{10}$ alkyl group or benzyl group; and $R^8$ is alkyl, or —$(CH_2)_k$—O-alkyl, wherein k is an integer of 1-30.

The progression of the reaction can be monitored by ESI-MS and/or NMR spectroscopy for consumption of the cationic monomer and epoxide. The reactions can be stopped at time when about >98% for the monomer and epoxide is consumed. The aqueous or alcoholic solution of the multiple charged cationic or anionic compounds can be used "as-is" for the application testing.

In the scheme described above, water and/or isopropanol can be used as solvent. However, the use of solvent and/or diluent for the reaction is optional. When employed, a wide range of non-acidic solvents are suitable, such as, for example, acetonitrile, ethers (e.g., tetrahydrofuran (THF)), other alcohols (e.g., methanol, ethanol, n-butanol, glycol, PEG, or a mixture) and the like In the scheme described above, no additional catalyst is necessary. Because the reactions to synthesize the disclosed multiple charged cationic or anionic compounds uses a polyamine, the polyamine itself can function as a (base) catalyst for both reactions. However, an additional catalyst is optional. Aza-Michael addition and ring-opening reactions employed for synthesis of the disclosed multiple charged cationic or anionic compounds can also be catalyzed by a strong acid or base.

In the scheme described above, the reactions can be carried at a temperature of from about 50° C. to about 130° C. However, the reaction temperature can range from about 20° C. to about 150° C., more preferably from about 50° C. to about 100° C.

In the scheme described above, synthesis is achieved in a two-step reaction. However, the disclosed multiple charged cationic or anionic compounds can be synthesized by one-step, one-pot reaction by tandem Michael addition and ring-opening reaction by reacting a polyamine simultaneously with the ionic monomers and epoxide.

Example 2

Synthesis of DETA/2EHGE (1:2) Adduct

To a 250 mL three necked round-bottom flask equipped with a temperature probe, condenser and magnetic stir bar was added 2-ethylhexyglycidal ether (2-EHGE, 55 grams). Diethylenetriamine (DETA, 15 grams) was then added to the well-stirred reaction mixture. Temperature of the reaction was increased to 130° C. and stirred for 3 hours or until completion of reaction.

Example 3

Synthesis of TEPA/$C_{12}$-$C_{14}$ alkylglycidyl ether (1:3) Adduct

To a 250 mL three necked round-bottom flask equipped with a temperature probe, condenser and magnetic stir bar was added ERISYS™ GE 8 ($C_{12}$-$C_{14}$ alkylglycidyl ether, CAS No: 68609-97-2, 132 grams). Triethylenepentamine (TEPA, 98%, 30 grams) was then added to the well-stirred reaction mixture. Temperature of the reaction was increased to 130° C. and stirred for 3 hours or until completion of reaction.

Example 4

Synthesis of TEPA/$C_{12}$-$C_{14}$ alkylglycidyl ether (1:2) Adduct

To a 250 mL three necked round-bottom flask equipped with a temperature probe, condenser and magnetic stir bar was added ERISYS™ GE 8 ($C_{12}$-$C_{14}$ alkylglycidyl ether, CAS No: 68609-97-2, 120 grams). Triethylenepentamine (TEPA, 98%, 40 grams) was then added to the well-stirred reaction mixture. Temperature of the reaction was increased to 130° C. and stirred for 3 hours or until completion of reaction.

Example 5

Synthesis of Ethyleneamine E-100/APTAC (1:2.5) Adduct

To a 250 mL three necked round-bottom flask equipped with temperature probe, condenser and magnetic stir bar were added polyethyleneamine E-100 (50 grams). (3-acrylamidopropyl)trimethylammonium chloride (APTAC, 75%, 121 grams), and water (20 grams) were then added into the flask. The resulting mixture was stirred at 80° C. overnight. As the reaction proceeded to completion, mixture turned into a clear yellowish solution.

Example 6

Synthesis of an Exemplary Multiple Charged Cationic Compound

To a 250 mL three necked round-bottom flask equipped with a temperature probe, condenser and magnetic stir bar was added the compound of Example 1 (DETA/2EHGE 1:2 adduct, 21.5 grams). 3-acrylamidopropyl)trimethylammonium chloride (APTAC, 75%, 34 grams,) and water were then added into the flask. The resulting suspension was stirred at 70° C. overnight or until complete consumption of APTAC was achieved. As the reaction proceeded to completion suspension turned into a clear yellowish solution.

Example 7

Synthesis of an Exemplary Multiple Charged Anionic Compound

To a 250 mL three necked round-bottom flask equipped with a temperature probe, condenser and magnetic stir bar was added the compound of Example 2 (DETA/2EHGE 1:2 adduct, 21.5 grams). 2-Acrylamido-2-methyl-1-propanesulfonic acid sodium salt solution (NaAMPS, 58%, 49 grams) and water (6 grams) were then added into the flask. The resulting suspension was stirred at 70° C. overnight or until complete consumption of NaAMPS was achieved. As the reaction proceeded to completion suspension turned into a clear yellowish solution.

Example 8

Synthesis of an Exemplary Multiple Charged Cationic Compound

To a 250 mL three necked round-bottom flask equipped with temperature probe, condenser and magnetic stir bar were added the compound of Example 3 (TEPA/$C_{12}$-$C_{14}$ alkylglycidyl ether, 1:3 adduct, 35.6 grams) and isopropanol (36 grams). (3-acrylamidopropyl)trimethylammonium chloride (APTAC, 75%, 24 grams) was then added into the flask. The resulting mixture was stirred at 70° C. overnight or until complete consumption of APTAC was achieved. As the reaction proceeded to completion suspension turned into a clear dark-amber solution.

Example 9

Synthesis of an Exemplary Multiple Charged Anionic Compound

To a 250 mL three necked round-bottom flask equipped with a temperature probe, condenser and magnetic stir bar were added the compound of Example 3 (TEPA/$C_{12}$-$C_{14}$ alkylglycidyl ether, 1:3 adduct, 40 grams) and isopropanol (26 grams). 2-Acrylamido-2-methyl-1-propanesulfonic acid sodium salt solution (NaAMPS, 58%, 46 grams) and water (31 grams) were then added into the flask. The resulting solution was stirred at 70° C. overnight or until complete consumption of NaAMPS was achieved. As the reaction proceeded to completion mixture turned into a clear yellowish solution.

Example 10

Synthesis of an Exemplary Multiple Charged Cationic Compound

To a 250 mL three necked round-bottom flask equipped with temperature probe, condenser and magnetic stir bar were added the compound of Example 4 (TEPA/$C_{12}$-$C_{14}$ alkylglycidyl ether, 1:2 adduct, 33.62 grams) and isopropanol (50 grams). 3-acrylamidopropyl)trimethylammonium chloride (APTAC, 75%, 31 grams) was then added into the flask. The resulting mixture was stirred at 70° C. overnight or until complete consumption of APTAC was achieved. As the reaction proceeded to completion suspension turned into a clear dark-amber solution.

Example 11

Synthesis of a Multiple Charged Cationic Compound/Surfactant

To a 250 mL three necked round-bottom flask equipped with a temperature probe, condenser and magnetic stir bar was added the compound of Example 5 (Ethyleneamine E-100/APTAC 1:2.5 adduct, 74%, 50 grams). ERISYS™ GE 8 ($C_{12}$-$C_{14}$ alkylglycidyl ether, CAS No: 68609-97-2, 41.5 grams) and isopropanol (40 grams) were then added into the flask. The resulting mixture was stirred at 90° C. overnight or until completion of reaction.

Example 12

Synthesis of a Multiple Charged Cationic Compound

To a 250 mL three necked round-bottom flask equipped with a temperature probe, condenser and magnetic stir bar was added the compound of Example 5 (Ethyleneamine E-100/APTAC 1:2.5 adduct, 74%, 63 grams). ERISYS™ GE 8 ($C_{12}$-$C_{14}$ alkylglycidyl ether, CAS No: 68609-97-2, 34.2 grams) and isopropanol (40 grams) were then added into the flask. The resulting mixture was stirred at 90° C. overnight or until completion of reaction.

Example 13

One Pot Synthesis of an Exemplary Multiple Charged Cationic Compound

To a 500 mL three necked round-bottom flask equipped with a temperature probe, condenser and magnetic stir bar were added ERISYS™ GE 8 ($C_{12}$-$C_{14}$ alkylglycidyl ether, CAS No: 68609-97-2, 110 grams), triethylenepentaamine (TEPA, 99%, 25 grams), 3-acrylamidopropyl)trimethylammonium chloride (APTAC, 75%, 108 grams) and isopropanol (80 mL). The resulting mixture was stirred at 90° C. overnight or until completion of the reaction as indicated by consumption of APTAC and ERISYS™ GE 8. As the reaction proceeded to completion mixture turned into a clear amber solution.

Example 14

One Pot Synthesis of an Exemplary Multiple Charged Cationic Compound

To a 500 mL three necked round-bottom flask equipped with a temperature probe, condenser and magnetic stir bar were added 2-ethylhexylglycidyl ether (98%, 93 grams), triethylenetetraamine (TETA, 60%, 29.8 grams), 3-acrylamidopropyl)trimethylammonium chloride (APTAC, 75%, 67 grams) and isopropanol (50 mL). The resulting mixture was stirred at 90° C. overnight or until completion of the reaction as indicated by consumption of APTAC and 2-ethylhexylglycidyl ether. As the reaction proceeded to completion mixture turned into a clear amber solution.

Example 15

One Pot Synthesis of an Exemplary Multiple Charged Anionic Compound

To a 500 mL three necked round-bottom flask equipped with a temperature probe, condenser and magnetic stir bar were added 2-ethylhexylglycidyl ether (98%, 77 grams), diethylenetriamine (DETA, 99%, 14 grams), acrylamido-2-methyl-1-propanesulfonic acid sodium salt solution (NaAMPS, 58%, 160 grams) and isopropanol (80 mL). The resulting mixture was stirred at 90° C. overnight or until completion of the reaction as indicated by consumption of NaAMPS and 2-ethylhexylglycidyl ether. As the reaction proceeded to completion mixture turned into a dark-yellow solution.

The disclosures being thus described, it will be obvious that the same may be varied in many ways. Such variations are not to be regarded as a departure from the spirit and scope of the disclosures and all such modifications are intended to be included within the scope of the following claims.

The above specification provides a description of the novel compounds, their synthesis and use, and the compositions, products, or articles that comprise the disclosed compounds. Since many embodiments can be made without departing from the spirit and scope of the disclosure, the disclosure resides in the claims.

What is claimed is:

1. A compound comprising:
   a compound derived from a polyamine through a reaction between the polyamine and an activated olefin and an epoxide, wherein the polyamine and activated olefin undergo aza Michael Addition reaction and the polyamine and epoxide undergo ring opening reaction;

wherein:
the activated olefin has one of the following formulas;

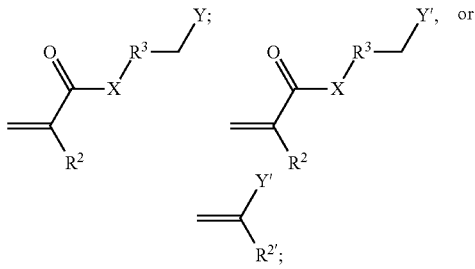

the epoxide is

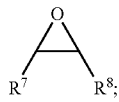

X is NH or O;
R$^2$ is H, CH$_3$, or an unsubstituted, linear or branched C$_2$-C$_{10}$ alkyl, alkenyl, or alkynyl group;
R$^{2'}$ is H, CH$_3$, or an unsubstituted or substituted, linear or branched C$_1$-C$_{10}$ alkyl, alkenyl, alkynyl group, —COOH, —CH$_2$COOH, Y', or —(CH$_2$)$_m$—Y', wherein m is an integer of 2 to 4;
R$^3$ is absent or an unsubstituted, linear or branched C$_1$-C$_{30}$ alkylene group;
Y is —NR$^4$R$^5$R$^{6(+)}$;
Y' is —COOH, —SO$_3$H, —PO$_3$H, —OSO$_3$H, —OPO$_3$H, or a salt thereof;
R$^4$, R$^5$, and R$^6$ are independently a C$_1$-C$_{10}$ alkyl group;
R$^7$ is H or alkyl; and
R$^8$ is alkyl, or —(CH$_2$)$_k$—O-alkyl, wherein k is an integer of 1-30;
wherein the compound is a multiple charged cationic compound having 1, 2, 3, or more positive charges from the activated olefin and at least one nonionic group from the epoxide, or a multiple charged anionic compound having 1, 2, 3, or more negative charges from the activated olefin and at least one nonionic group from the epoxide.

2. The compound according to claim 1, wherein the polyamine is (i) a linear, branched, or dendrimer polyamine with a general formula of —[RNH]$_n$—, where in R is —CH$_2$—, —CH$_2$CH$_2$—, —CH$_2$CH$_2$CH$_2$—, —CH(CH$_3$)CH$_2$—, a linear or branched, unsubstituted or substituted C$_2$-C$_{10}$ alkylene group, or combination thereof and n is an integer of 1, 2, 3, 4, 5, 6, 7, 8, 9, or 10 to 1,000,000; (ii) a linear polyamine with a general formula of H$_2$N—(RNH)$_n$—RNH$_2$, where in R is —CH$_2$—, —CH$_2$CH$_2$—, —CH$_2$CH$_2$CH$_2$—, —CH(CH$_3$)CH$_2$—, a linear or branched, unsubstituted or substituted C$_2$-C$_{10}$ alkylene group, or combination thereof and n is an integer of 1, 2, 3, 4, 5, 6, 7, 8, 9, or 10 to 1,000,000; or (iii) a linear polyamine with a general formula of H$_2$N—(RN(R'))$_n$—RNH$_2$, where in R is —CH$_2$—, —CH$_2$CH$_2$—, —CH$_2$CH$_2$CH$_2$—, —CH(CH$_3$)CH$_2$—, a linear or branched, unsubstituted or substituted C$_2$-C$_{10}$ alkylene group, or combination thereof, R' is —CH$_2$—, —CH$_2$CH$_2$—, —CH$_2$CH$_2$CH$_2$—, —CH(CH$_3$)CH$_2$—, a linear or branched, unsubstituted or substituted C$_2$-C$_{10}$ alkyl group, RNH$_2$, RNHRNH$_2$, or RN(RNH$_2$)$_2$ and n is an integer of 1, 2, 3, 4, 5, 6, 7, 8, 9, or 10 to 1,000,000.

3. The compound according to claim 1, wherein the polyamine is a polyalkyleneimine selected from the group consisting of ethyleneimine, propyleneimine, butyleneimine, pentyleneimine, hexyleneimine, heptyleneimine, and a combination thereof.

4. The compound according to claim 1, wherein the polyamine is an alkyleneamine selected from the group consisting of ethylenediamine, diethylenetriamine, triethylenetetramine, tetraethylenepentamine, pentaethylenehexamine, hexaethyleneheptamine, polyethyleneimine, tris(2-aminoethyl)amine, and a combination thereof.

5. The compound according to claim 1, wherein the polyamine is a mixture of monoamine, diamine, and triamine with a polyether backbone or with a polyether backbone based on propylene oxide (PO), ethylene oxide (EO), or a mixture of both oxides.

6. The compound according to claim 1, wherein the polyamine is a linear, branched, or dendrimer polyethyleneimine.

7. The compound according to claim 1, wherein the polyamine comprises (i) only primary and secondary amine groups, (ii) only primary, secondary, and tertiary amine groups, or (iii) only primary and tertiary amine groups.

8. The compound according to claim 1, wherein the polyamine is a single compound, or is a mixture of two or more different polyamines, wherein the different polyamines have different molecular weight, different structure, or both.

9. The compound according to claim 1, wherein the polyamine has an average molecular weight of from about 60 to about 2,000,000 Da.

10. The compound according to claim 1, wherein X is NH or O and R$^2$ is H or CH$_3$.

11. The compound according to claim 1, wherein Y is (i) —NR$^4$R$^5$R$^{6(+)}$, and R$^4$, R$^5$, and R$^6$ are independently CH$_3$, (ii) —NR$^4$R$^5$R$^{6(+)}$, R$^4$ and R$^5$ are independently CH$_3$, and R$^6$ is a C$_2$-C$_{12}$ aromatic alkyl, (iii) —NR$^4$R$^5$R$^{6(+)}$, R$^4$ and R$^5$ are independently CH$_3$, and R$^6$ is —CH$_2$—C$_6$H$_6$, or (iv) —NR$^4$R$^5$R$^{6(+)}$ and the counter ion for Y is chloride, bromide, fluoride, iodide, acetate, aluminate, cyanate, cyanide, dihydrogen phosphate, dihydrogen phosphite, formate, hydrogen carbonate, hydrogen oxalate, hydrogen sulfate, hydroxide, nitrate, nitrite, thiocyanate, or a combination thereof.

12. The compound according to claim 1, wherein Y' is —COOH or salt thereof, —SO$_3$H or salt thereof, or —PO$_3$H or salt thereof.

13. The compound according to claim 1, wherein R$^3$ is CH$_2$, —CH$_2$CH$_2$—, —CH$_2$CH$_2$CH$_2$—, —C(CH$_3$)$_2$—, an unsubstituted, linear, and saturated C$_1$-C$_{20}$ alkylene group, an unsubstituted, linear, and unsaturated C$_1$-C$_{20}$ alkylene group, a linear C$_8$-C$_{18}$ alkyl, alkenyl, or alkynyl group, or a branched C$_8$-C$_{20}$ alkyl, alkenyl, or alkynyl group.

14. The compound according to claim 1, wherein (i) R$^8$ is H and R$^7$ is C$_1$-C$_{30}$ alkyl, (ii) R$^8$ is C$_1$-C$_{30}$ alkyl and R$^7$ is H, CH$_3$, or C$_2$-C$_4$ alkyl, or (iii) R$^8$ is C$_4$-C$_{30}$ alkyl or C$_8$-C$_{20}$ alkyl.

15. The compound according to claim 1, wherein the epoxide is an alkylglyicdal ether, butylglycidal ether, hexylglycidal ether, octylglycidal ether, dodecyglycidal ether, tetradecylglycidal ether a 1,2-epoxyalkane, 1,2-epoxytertadecane, 1,2-epoxydodecane, or 1,2-epoxyoctane, and wherein the activated olefin is (3-acrylamidopropyl)trimethylammonium chloride (APTAC), [3-(Methacryloylamino)propyl]trimethylammonium chloride (MAPTAC), 2-(acryloyloxy)-N,N,N-trimethylethanaminium chloride (DMAEA-MCQ), N,N-dimethylaminoethyl acrylate benzyl chloride quaternary salt (DMAEA-BCQ), or 2-(methacryloyloxy)-N,N,N-trimethylethan-1-aminium methyl sulfate (DMAEA-MSQ).

16. The compound according to claim 1, wherein the activated olefin is an acrylic acid, methacrylic acid, 2-acrylamido-2-methylpropane sulfonic acid (AMPS), itaconic acid, maleic acid, or 3-(allyloxy)-2-hydroxypropane-1-sulfonate.

17. The compound according to claim 1, wherein the activated olefin is vinylsulfonic acid, vinylphosphonic acid, or mixture thereof.

18. The compound according to claim 1, wherein Y' is anionic group, the positive counter ion is $Li^+$, $Na^+$, $K^+$, $NH_3^+$, or a quaternary ammonium.

19. The compound according to claim 1, wherein the compound is a mixture of at least two modified polyamine compounds derived from the same polyamine, activated olefin, and epoxide, or wherein the compound is a mixture of at least two modified polyamine compounds derived from different polyamines and the same activated olefin and epoxide.

20. The compound according to claim 1, wherein the compound has an average molecular weight ($M_w$) of from about 100 to about 2,000,000 Da.

21. The compound according to claim 1, wherein the compound has at least 2 positive charges; or at least 4 negative (anionic) charges.

22. The compound according to claim 1, wherein the compound has one of the generic formula of $NA_2$-$[R^{10'}]_n$-$NA_2$, $(RNA)_n$-$RNA_2$, $NA_2$-$(RNA)_n$-$RNA_2$, or $NA_2$-$(RN(R'))_n$—$RNA_2$, wherein:

R$^{10'}$ is a linear or branched, unsubstituted or substituted $C_4$-$C_{10}$ alkylene group, or combination thereof;

R is —$CH_2$—, —$CH_2CH_2$—, —$CH_2CH_2CH_2$—, —CH($CH_3$)$CH_2$—, a linear or branched, unsubstituted or substituted $C_4$-$C_{10}$ alkylene group, or combination thereof;

R' is —$CH_2$—, —$CH_2CH_2$—, —$CH_2CH_2CH_2$—, —CH($CH_3$)$CH_2$—, a linear or branched, unsubstituted or substituted $C_4$-$C_{10}$ alkyl group, $RNA_2$, $RNARNA_2$, or $RN(RNA_2)_2$;

n can be from 1 to 1,000,000;

A is a combination of H,

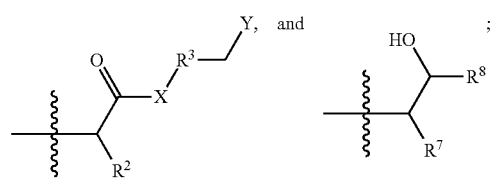

or a combination of H,

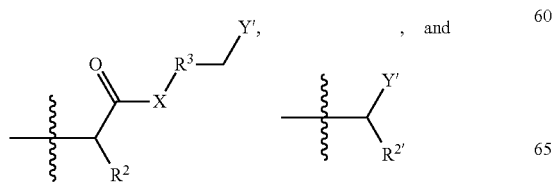

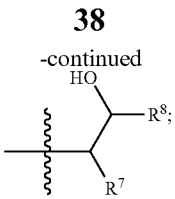

X is NH or O;

R$^2$ is H, $CH_3$, or an unsubstituted, linear or branched $C_2$-$C_{10}$ alkyl, alkenyl, or alkynyl group;

R$^{2'}$ is H, $CH_3$, or an unsubstituted or substituted, linear or branched $C_1$-$C_{10}$ alkyl, alkenyl, alkynyl group, —COOH, —$CH_2COOH$, Y', or —$(CH_2)_m$—Y'; m is an integer of 2 to 4;

R$^3$ is absent or an unsubstituted, linear $C_1$-$C_{30}$ alkylene group;

R$^{3'}$ is absent or an unsubstituted, linear or branched $C_1$-$C_{30}$ alkylene group;

Y is —$NR^4R^5R^{6(+)}$;

Y' is —COOH, —$SO_3H$, —$PO_3H$, —$OSO_3H$, —$OPO_3H$, or a salt thereof;

R$^4$, R$^5$, and R$^6$ are independently a $C_1$-$C_{10}$ alkyl group;

R$^7$ is H or alkyl; and

R$^8$ is alkyl, or —$(CH_2)_k$—O-alkyl, wherein k is an integer of 1-30;

wherein the compound is a multiple charged cationic compound having 1, 2, 3, or more

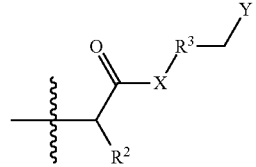

groups and at least one

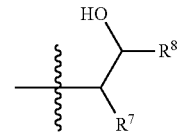

group or a multiple charged anionic compound having 1, 2, 3, or more

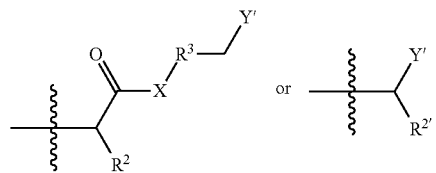

groups, and at least one

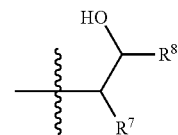

group.

23. The compound according to claim 1, wherein the compound is derived from a linear polyethyleneimine and 2-acrylamido-2-methyl-1-propanesulfonic acid and $C_{12}$-$C_{14}$ alkylglycidyl ether.

24. The compound according to claim 1, wherein the compound is from a branched polyethyleneimine and 2-ethylhexyglycidal ether and (3-acrylamidopropyl)trim ethyl ammonium chloride (APTAC).

25. The compound according to claim 1, wherein the compound has at least 10 positive (or cationic) charges; or at least 10 negative (anionic) charges.

* * * * *

UNITED STATES PATENT AND TRADEMARK OFFICE
CERTIFICATE OF CORRECTION

Page 1 of 2

PATENT NO. : 11,236,040 B2
APPLICATION NO. : 16/554415
DATED : February 1, 2022
INVENTOR(S) : Ashish Dhawan and Carter M. Silvernail It is certified that error appears in the above-identified patent and that said Letters Patent is hereby corrected as shown below:

In the Claims

In Column 35, Claim 2, Line 51:
DELETE: "where in" before "R"
INSERT: --wherein-- before "R"

In Column 35, Claim 2, Line 57:
DELETE: "where in" before "R"
INSERT: --wherein-- before "R"

In Column 35, Claim 2, Line 62:
DELETE: "where in" before "R"
INSERT: --wherein-- before "R"

In Column 36, Claim 15, Line 60:
DELETE: "alkylglyicdal"
INSERT: --alkylglycidyl--

In Column 36, Claim 15, Line 60:
DELETE: "butylglycidal"
INSERT: --butylglycidyl--

In Column 36, Claim 15, Lines 60-61:
DELETE: "hexylglycidal"
INSERT: --hexylglycidyl--

In Column 36, Claim 15, Line 61:
DELETE: "octylglycidal"
INSERT: --octylglycidyl--

Signed and Sealed this
Twenty-eighth Day of June, 2022

Katherine Kelly Vidal
*Director of the United States Patent and Trademark Office*

CERTIFICATE OF CORRECTION (continued)
U.S. Pat. No. 11,236,040 B2

In Column 36, Claim 15, Line 61:
DELETE: "dodecyglycidal"
INSERT: --dodecylglycidyl--

In Column 36, Claim 15, Line 62:
DELETE: "tetradecylglycidal ether"
INSERT: --tetradecylglycidyl ether,--

In Column 36, Claim 15, Line 62-63:
DELETE: "1,2-epoxytertadecane,"
INSERT: --1,2-epoxytetradecane,--

In Column 39, Claim 24, Lines 6-7:
DELETE: "2-ethylhexyglycidal" after "and"
INSERT: --2-ethylhexylglycidyl-- after "and"

In Column 39, Claim 24, Line 7:
DELETE: "(3-acrylamidopropyl)trim ethyl" after "and"
INSERT: --(3-acrylamidopropyl)trimethylammonium-- after "and"